US008088740B2

(12) United States Patent
Hur et al.

(10) Patent No.: US 8,088,740 B2
(45) Date of Patent: Jan. 3, 2012

(54) GOLD BINDING PEPTIDES AND SHAPE-AND SIZE-TUNABLE SYNTHESIS OF GOLD NANOSTRUCTURES

(75) Inventors: Hor Gil Hur, Gwangju (KR); Jung Ok Kim, Gwangju (KR); Dae Hee Kim, Gwangju (KR); No Sang Myung, Riverside, CA (US)

(73) Assignee: Gwangju Institute of Science and Technology, Gwangju (KR)

( * ) Notice: Subject to any disclaimer, the term of this patent is extended or adjusted under 35 U.S.C. 154(b) by 338 days.

(21) Appl. No.: 12/387,501

(22) Filed: May 4, 2009

(65) Prior Publication Data

US 2010/0280220 A1    Nov. 4, 2010

(51) Int. Cl.
*A61K 38/10* (2006.01)
*A61K 33/24* (2006.01)
*A01N 55/02* (2006.01)

(52) U.S. Cl. ........ 514/21.5; 514/495; 977/773; 424/649

(58) Field of Classification Search .................. None
See application file for complete search history.

(56) References Cited

OTHER PUBLICATIONS

Hnilova, 2008, Langmuir, 24, 12440-12445.*
Baesman et al., "Formation of Tellurium Nanocrystals During Anaerobic Growth of Bacteria That Use Te Oxyanions as Respiratory Electron Acceptors," Appl. Environ. Microbiol. 73:2135-2143, 2007.
Brown et al., "A Genetic Analysis of Crystal Growth," J. Mol. Biol. 299:725-735, 2000.
Klonowska et al., "Selenite and Tellurite Reduction by *Shewanella oneidensis*," Appl. Environ. Microbiol. 71:5607-5609, 2005.
Lee et al., "Biogenic Formation of Photoactive Arsenic-Sulfide Nanotubes by *Shewanella* sp. Strain HN-41," Proc. Natl. Acad. Sci. U.S.A. 104:20410-20415, 2007.
Sarikaya et al., "Molecular Biomimetics: Nanotechnology Through Biology," Nature 2:577-585, 2003.

\* cited by examiner

*Primary Examiner* — Cecilia J Tsang
*Assistant Examiner* — Satyanarayana Gudibande
(74) *Attorney, Agent, or Firm* — Clark & Elbing LLP

(57) ABSTRACT

The present invention relates to gold binding peptides and shape- and size-tunable synthesis of gold nanostructures. The present inventions are very useful for the production of well-designed, gold-based architectures. The size- and shape-specific gold nanostructure materials prepared by the present invention may find use as: highly conductive interconnections for single-electron transistors, catalysts for the oxidation of carbon monoxide; biological and chemical sensors; and as contrasting agents for electron microscopic and medical imaging applications.

5 Claims, 28 Drawing Sheets

(2 of 28 Drawing Sheet(s) Filed in Color)

TEM images of gold nanostructures formed by Midas peptides

Fig. 4

| Peptides | Amino acid sequences |
|---|---|
| (a) Midas-1 | GGTSV LIATP YV |
| (b) Midas-4 | TGTSV LIATP YV |
| (c) Midas-7 | TGTSV LGATP YV |
| (d) Midas-8 | TGTSV LIGTP YV |
| (e) Midas-9 | TGTSV LIAGP YV |
| (f) Midas-10 | TGTSV LIATG YV |
| (g) Midas-12 | TGTSV LIATP YG |

# GOLD BINDING PEPTIDES AND SHAPE- AND SIZE-TUNABLE SYNTHESIS OF GOLD NANOSTRUCTURES

BACKGROUND OF THE INVENTION

1. Field of the Invention

The present invention relates to gold binding peptides and shape- and size-tunable synthesis of gold nanostructures.

2. Description of the Related Art

Recent advances in nanotechnology and heightened concern for the environmental impact of nanoscale materials requires the development of environmentally benign methods to synthesize nanostructures with controlled morphology and architecture. The size and shape of nanomaterials has a major influence on their physical and chemical properties and the ability to control these parameters remains a great technological challenge with important implications in nanoscale science and engineering[1]. Over the last 30 years[2] several chemical synthesis methods have been developed to produce semiconducting and metallic nanostructures and several studies have demonstrated that their size-dependent properties are due to quantum confinement effect[3]. The shape and size of nanostructures are generally controlled by using hard templates or soft direct agents, including organic surfactants and polymers. The chemical synthesis of nanostructures, however, has several major drawbacks, including the use of toxic chemicals and extreme synthesis conditions involving high operating temperatures and pressure, and highly acidic or alkaline reaction conditions.

In contrast, several natural biological systems have been shown to produce inorganic materials under physiological conditions that have intricate nano-architectures and superior multi-functional properties. These biologically-synthesized materials include the zero- and three-dimensional nanostructures of magnetite[4], metal sulfides[5], selenium[6], tellurium[7], gold[8], and silver[9] and the one-dimensional nanostructures found in tellurium nanorods[10] and arsenic sulfide nanotubes[11]. Relative to chemical routes, biological systems appear to be extremely adept at directing the synthesis and assembly of inorganic nanostructures to create hierarchical nanostructures at near ambient conditions, in environmentally compatible solutions, and utilizing eco-friendly reducing and capping agents[12].

Engineered peptides that recognize inorganic surfaces have been shown to be useful for the assembly and synthesis of inorganic nanostructures[13]. For example, Brown et al. used gold binding polypeptides (GBP1), initially identified in a cell-surface display library, to synthesize nanometer thick platelets and nanoparticles of gold, suggesting the feasibility of synthesizing inorganic nanostructures using genetically engineered peptides[14]. Similarly, Xie et al. isolated a protein from the unicellular green alga *Chlorella vulgars* that formed nanometer thick gold platelets with high yield[12]. The size of platelets, which was defined as the longest possible width, was less than 0.1 mm[15]. Despite the variety of structures produced by biological systems, engineering applications frequently require uniformly precise nanomaterials with exacting and specific dimensional characteristics.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel peptides useful for the production of well-designed, gold-based architectures and to discover the mechanism controlling the size and shape of nano- and micron-size particles, which is a critical step for biosynthesis routes, remains elusive. As results, the present inventors have found novel peptides having binding affinity to gold and capability of producing gold nanostructure in shape- and size-tunable manner.

Accordingly, it is an object of the present invention to provide a peptide binding affinity to gold and capability of producing gold nanostructure in shape- and size-tunable manner.

It is another object of this invention to provide a method for preparing a gold nanostructure.

It is still another object of this invention to provide a method for preparing a gold nanostructure in shape- or size-tunable synthesis manner.

Other objects and advantages of the present invention will become apparent from the following detailed description together with the appended claims and drawings.

BRIEF DESCRIPTION OF THE DRAWINGS

The application file contains drawings executed in color (FIGS. 7 and 12C). Copies of this patent or patent application with color drawings will be provided by the Office upon request and payment of the necessary fee.

FIG. 4 shows TEM images of the synthesized gold nanostructures by peptides (0.2 mg/ml) Midas-1 (SEQ ID NO: 1) (a), Midas-4 (SEQ ID NO: 4) (b), Midas-7 (SEQ ID NO: 7) (c), Midas-8 (SEQ ID NO: 8) (d), Midas-9 (SEQ ID NO: 9) (e), Midas-10 (SEQ ID NO: 10) (f) and Midas-12 (SEQ ID NO: 12) (g) in deionized water at pH 3 and 37° C.

DETAILED DESCRIPTION OF THIS INVENTION

Figure 1A:
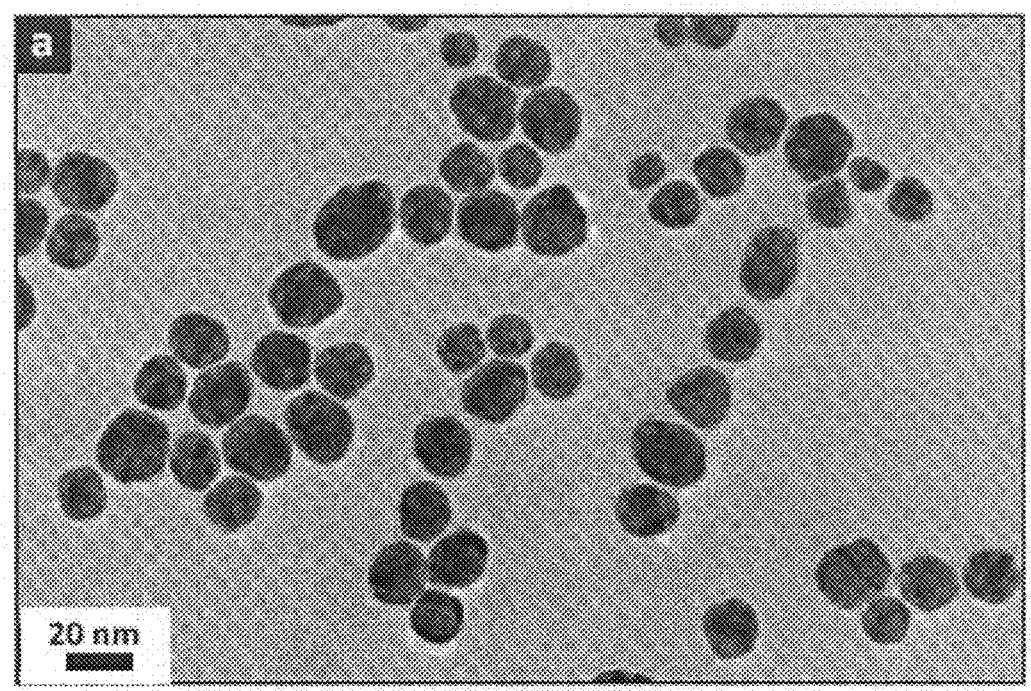
FIG. 1A-1C represent TEM image (FIG. 1A (a)), UV-Vis spectra (FIG. 1B (b)), and average size (FIG. 1C (c)) of gold nanostructures synthesized in 3 days by peptide Midas-2 (0.2 mg/ml) at room temperature in phosphate buffer at pH 7.12 after adding 0.5 mM of $HAuCl_4$ (counting 265 particles).

In one aspect of the present invention, there is provided a peptide comprising the amino acid sequence selected from the group consisting of SEQ ID NOs:1-30.

The present inventors have made intensive researches to develop novel peptides useful for the production of well-designed, gold-based architectures and to discover the mechanism controlling the size and shape of nano- and micron-size particles, which is a critical step for biosynthesis routes, remains elusive. As results, the present inventors have found novel peptides having binding affinity to gold and capability of producing gold nanostructure in shape- and size-tunable manner.

The peptides of the present invention bind to gold ions and then induce the reduction of gold ions.

Preferably, the peptide of the present invention consists essentially of the amino acid sequence of SEQ ID NOs:1-30.

Most Preferably, the peptide consists of the amino acid sequence of SEQ ID NOs:1-30.

According to a preferred embodiment, the present invention is a peptide comprising the amino acid sequence selected from the group consisting of SEQ ID NOs:1-12.

The term used herein "peptide" refers to a linear molecule formed by linking amino acid residues through peptide bonds.

The peptides of the invention may be prepared by conventional chemical synthesis processes known to one of skill in the art, in particular, solid-phase synthesis techniques (Merrifield, *J. Amer. Chem. Soc.* 85:2149-54(1963); Stewart, et al., *Solid Phase Peptide Synthesis,* 2nd. ed., Pierce Chem. Co.: Rockford, 111(1984)). The peptides of the invention may be also provided by a phage display technology (Smith G P "Filamentous fusion phage: novel expression vectors that display cloned antigens on the virion surface". *Science* 228 (4705):1315-1317(1985); Smith G P, Petrenko Va. "Phage display". *Chem. Rev.* 97(2):391-410(1997)). In addition, the peptides of this invention may be prepared in accordance with gene cloning methods. More specifically, the nucleotide sequences coding for the gold-binding peptide are transformed into suitable host cells and expressed to produce the gold-binding peptide (see Sambrook, J. et al., *Molecular Cloning. A Laboratory Manual,* 3rd ed. Cold Spring Harbor Press (2001)).

The gold-binding peptides of the present invention include peptides in which one or more of amino acids have side chain modification. Examples of side chain modifications include modifications of amino groups such as by reductive alkylation; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal. The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues must not affect the ability of the peptide to form the necessary disulphide bonds. It is also possible to replace the sulphydryl group of cysteine with selenium equivalents such that the peptide forms a diselenium bond in place of one or more of the disulphide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Proline residue may be modified by, for example, hydroxylation in the 4-position.

In another aspect of this invention, there is provided a method for preparing a gold nanostructure, comprising contacting a gold salt to a peptide comprising the amino acid sequence selected from the group consisting of SEQ ID NOs: 1-30.

Since the present method utilizes the peptides of the present invention describe above, the common descriptions between them are omitted in order to avoid undue redundancy leading to the complexity of this specification.

The gold ions are reduced by the gold-binding peptide of the present invention, resulting in production of gold nanostructure. In a preferred embodiment, the production of gold nanostructures may be achieved by simple incubating the gold salt with the gold-binding peptide.

According to a preferred embodiment, the present peptide used in the present invention is a peptide comprising the amino acid sequence selected from the group consisting of SEQ ID NOs:1-12.

The present method may be carried out by incubating a gold salt to the gold-binding peptide under suitable conditions. Preferably, reaction temperature is 20-45° C., more preferably, 30-40° C., most preferably about 37° C. The reaction time preferably ranges from 10 to 200 hr, more preferably from 50-100 hr, most preferably about 72 hr.

The gold salt used in the invention includes any gold salt to produce gold particles. Preferred gold salts used in methods of the invention include $HAuCl_4$, $NaAuCl_4$, most preferably, $HAuCl_4$.

Preferably, the concentration of the gold salt ranges from 0.01 mM to 100 mM, more preferably, from 0.1 mM to 80 mM, most preferably from 0.2-50 mM.

Preferably, the pH of the reaction is 1.0-10.0, more preferably 3.0-9.0, still more preferably 5.0-8.0, most preferably 7.0-7.8.

The nanostructure finally produced by the present invention depends on types of gold-binding peptides and reaction conditions used. Preferably, the nanostructure produced by the present method is nanoparticle, nanoplate, nanoribbon, nanowire, nanorod, nanotube or nanodot, more preferably, nanoparticle, nanoplate, nanoribbon or nanowire.

In still another aspect of this invention, there is proved a method for preparing a gold nanostructure in shape- or size-tunable synthesis manner, comprising the steps of:
 (a) providing a gold-binding peptide;
 (b) substituting at least one amino acid residue of the gold-binding peptide with an amino acid; and
 (c) contacting a gold salt to the substituted gold-binding peptide.

Since the present method follows the method for preparing a gold nanostructure of this invention, the common descriptions between them are omitted in order to avoid undue redundancy leading to the complexity of this specification.

Interestingly, the present inventors have found that amino acid change in gold-binding peptides contributes to shape- or size-tunable synthesis of gold nanostructures.

The gold-binding proteins may be screened by a phage display technology and prepared by conventional solid phase synthesis or gene cloning technologies as described previously.

According to a preferred embodiment, the gold-binding peptide is a peptide comprising the amino acid sequence selected from the group consisting of SEQ ID NOs:1-30, more preferably SEQ ID NOs:1-12.

According to a preferred embodiment, the amino acid residue substituted with other amino acids is the $11^{th}$ amino acid of SEQ ID NOs:1-12.

According to a preferred embodiment, the step (c) is carried out under a changed reaction condition; in which the reaction condition is temperature, pH or a concentration of the gold salt.

The reaction conditions are also responsible for shape and size of gold nanostructures prepared by the present method.

The size- and shape-specific gold nanostructure materials prepared by the present invention may find use as: highly conductive interconnections for single-electron transistors, catalysts for the oxidation of carbon monoxide; biological and chemical sensors; and as contrasting agents for electron microscopic and medical imaging applications.

The present invention will now be described in further detail by examples. It would be obvious to those skilled in the art that these examples are intended to be more concretely illustrative and the scope of the present invention as set forth in the appended claims is not limited to or by the examples.

Examples

Materials and Methods

Chemicals and Peptides $HAuCl_4.3H_2O$ and metallic gold powder were purchased from Aldrich (St. Louis, Mo.). Sodium hydroxide and hydrochloric acid solution were purchased from Fisher Scientific (Pittsburgh, Pa.). Nanopure water used was prepared by the Milli-Q system from Millipore (Millipore, Billerica, Mass.) and autoclaved to avoid extra microbial contamination. All reagents were used as received with no further purification steps. All peptides used were purchased from AnyGen Co. Ltd. (Gwangju, Korea).

Isolation of Gold Binding Peptides

A random phage display peptide library was purchased from New England BioLab (Ph.D.-12 phage display peptide library kit, MA, USA). All steps for isolating gold-binding peptide were followed by manufacturer's instruction. However, metallic gold powder in an Eppendorf tube was directly used as target materials for isolation of binding phages instead of a substrate coated with a target materials or solution of phage with a target attached by affinity tags.

Shortly, isolation of gold-binding peptides was carried out by panning (target binding and elution), titering, amplification and sequencing. Target metallic gold powder were washed three times with Tris-buffered saline containing 0.1% Tween-20 (TBST). Diluted $4\times10^{10}$ of phage in 1 ml of TBST was then added in the solution of washed metallic gold powder. After incubating for 1 hour at room temperature, reacted sample was washed ten times with TBST buffer and phages bound to metallic gold powder were eluted by addition of Glycine-HCl (pH 2.2). Supernatant including phages was neutralized by adding Tris-HCl (pH 9.1). Eluted phages were tittered and amplified by infection of *Escherichia coli* ER2537. Phages binding on the surface of particles were separated by 20% (w/v) polyethylene glycol-8000 with 2.5 M NaCl (PEG/NaCl). Titeration and amplification were performed repeatedly during steps of two additional rounds of panning. Infected *E. coil* ER2537 on the plate of Luria broth (LB) media containing 5-bromo-4-chloro-3-indoyl-β-D-galadosidase (X-Gal) and isopropyl-β-D-thiogalacosidase (IPTG) were isolated by the blue color of plaque which indicates the expression of phage gene. Then, single strand of phage DNA was purified and sequenced.

Change in Primary Structure of Gold Nanostructure Synthesizing Peptide

A gold binding and synthesizing peptide, which has 12 amino acids (TGTSVLIATPYV; SEQ ID NO: 2) obtained by the combinatorial peptide phage display techniques, was named as Midas-2. In order to investigate the role of each amino acid in Midas-2 on synthesis of gold nanostructures, 12 different Midas peptides were synthesized substituting each amino acid of Midas-2 with glycine as indicated in Table 1.

TABLE 1

Amino acid sequences of 12 different Midas peptides

| Peptides | Sequences |
|---|---|
| Midas-2 (SEQ ID NO: 2) | T G T S V L I A T P Y V |
| Midas-1 (SEQ ID NO: 1) | G G T S V L I A T P Y V |
| Midas-3 (SEQ ID NO: 3) | T G G S V L I A T P Y V |
| Midas-4 (SEQ ID NO: 4) | T G T G V L I A T P Y V |
| Midas-5 (SEQ ID NO: 5) | T G T S G L I A T P Y V |
| Midas-6 (SEQ ID NO: 6) | T G T S V G I A T P Y V |
| Midas-7 (SEQ ID NO: 7) | T G T S V L G A T P Y V |
| Midas-8 (SEQ ID NO: 8) | T G T S V L I G T P Y V |
| Midas-9 (SEQ ID NO: 9) | T G T S V L I A G P Y V |
| Midas-10 (SEQ ID NO: 10) | T G T S V L I A T G Y V |
| Midas-11 (SEQ ID NO: 11) | T G T S V L I A T P G V |
| Midas-12 (SEQ ID NO: 12) | T G T S V L I A T P Y G |

In addition to the glycine scanning in Midas-2, glycine located at $11^{th}$ position in the peptide Midas-11 was replaced with other 19 amino acids, named Midas-11$_{Amino\ Acid}$.

Synthesis of Gold Nanostructures by Midas Peptides

Midas-2 in 0.2 mg/ml was dissolved in phosphate buffer (10 mM, pH 7.5). HAuCl$_4$ was added to the solution in the final concentration of 0.5 mM and the final reaction volume was adjusted to 1 ml and incubated at room temperature under dark conditions for 3 days. In order to remove any possibility of the solute in the phosphate buffer on the formation of gold nanostructures, deionized water was used instead of the phosphate buffer and incubated at 37° C. To investigate the effect of pH on the gold nanostructure synthesis by peptide Midas-11, initial pH condition was adjusted with 5 M NaOH and concentrated HCl prior to addition of the peptide solution into deionized water containing HAuCl$_4$. pH condition was fixed at 1.0, 3.0, 4.5, 5.7, 8.1, and 9.0 with 0.5 mM HAuCl$_4$, and 1.0, 1.7, 3.0, 5.0, 5.4, and 7.0 with 30 mM HAuCl$_4$. The gold ions remained in supernatant of the reaction solutions were measured using AAnalyst 800 (PerkinElmer, Waltham, Mass.) after the supernatant was centrifuged and diluted with 10% of HCl solution.

Structural Characterization of Synthesized Gold Nanostructures

Synthesized gold nanostructures were collected by centrifugation (Centrifuge 5415D, Eppendorf, Fisher Scientific, Pittsburgh, Pa.) at 9,300 rcf for 10 min at room temperature, washed 2 times with autoclaved deionized water, and re-suspended with 1 ml for surface plasmon resonance analysis using UV-visible spectrophotometer (Shimadzu, Kyoto, Japan). For the structural analyses using scanning electron microscopy, transmission electron microscopy/energy dispersive X-ray spectroscopy and atomic force microscopy, the washed gold nanostructures were dispersed in 100 μL deionized water. The samples for SEM analyses were prepared by placing ~5 μL of the suspension and drying in the air on a silicon wafer. Secondary SEM images were performed by SEM/E-beam lithography system (Leo SUPRA 55, Carl Zeiss, Germany) and an accelerating voltage was fixed at 10 kV. The SEM samples were also subjected to AFM analyses. AFM images were obtained using Innova Scanning Prove Microscope (Veeco, Plainview, N.Y.). TEM analyses were conducted on a FEI CM300 TEM (Philips, Briarcliff Manor, N.Y.) at an accelerating voltage of 300 kV. The samples were prepared by depositing a droplet of water suspension of the gold crystals onto carbon-coated Cu support grids that were subsequently dried in air. Selected area electron diffraction (SAED), conventional bright- and dark-field as well as high-resolution imaging were utilized to study the size, shape, distribution, and crystallographic orientation of the gold particles and their aggregates.

Temperature Dependent Electrical Resistance

The electrical resistance properties at temperatures range between 10 to 300 K were measured using Delta Mode System (Keithley 6221 AC/DC Current Source and 2182A Nanovoltmeter) with ±2 nA applied current, and cold-finger cryogenic system (Janis CCS-350SH).

Results and Discussion

Figure 1B:
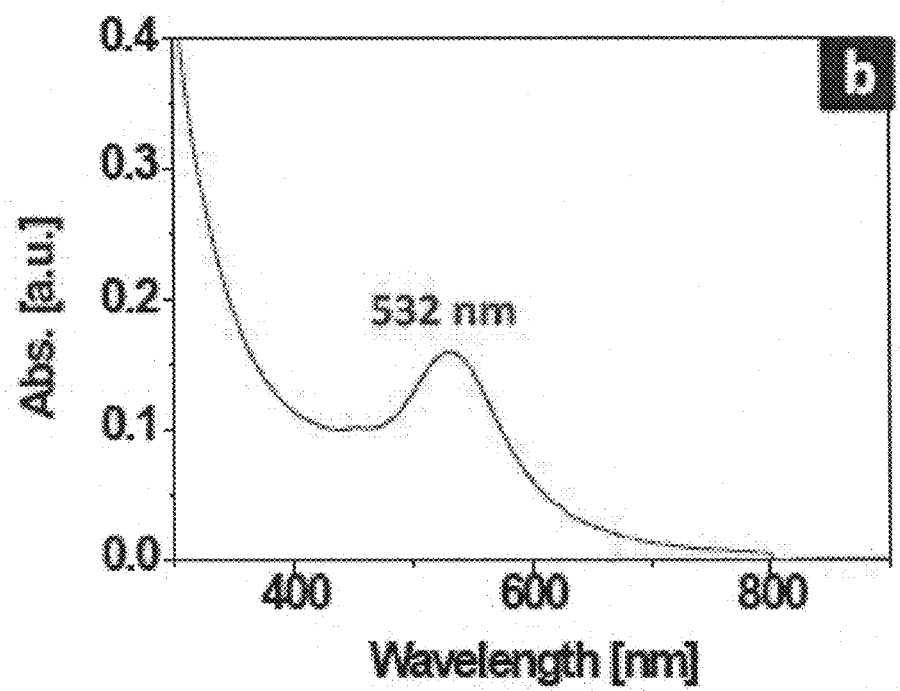
Figure 1C:
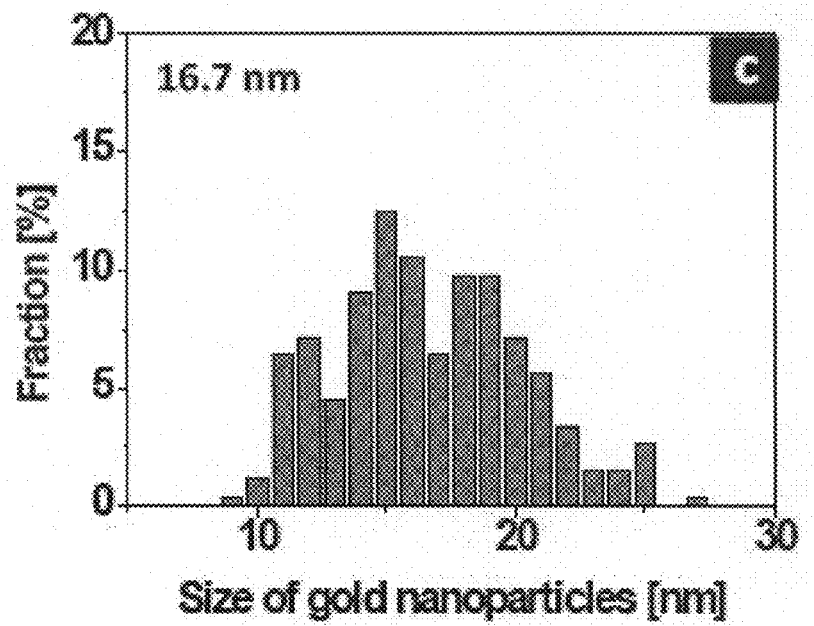
Figure 2:
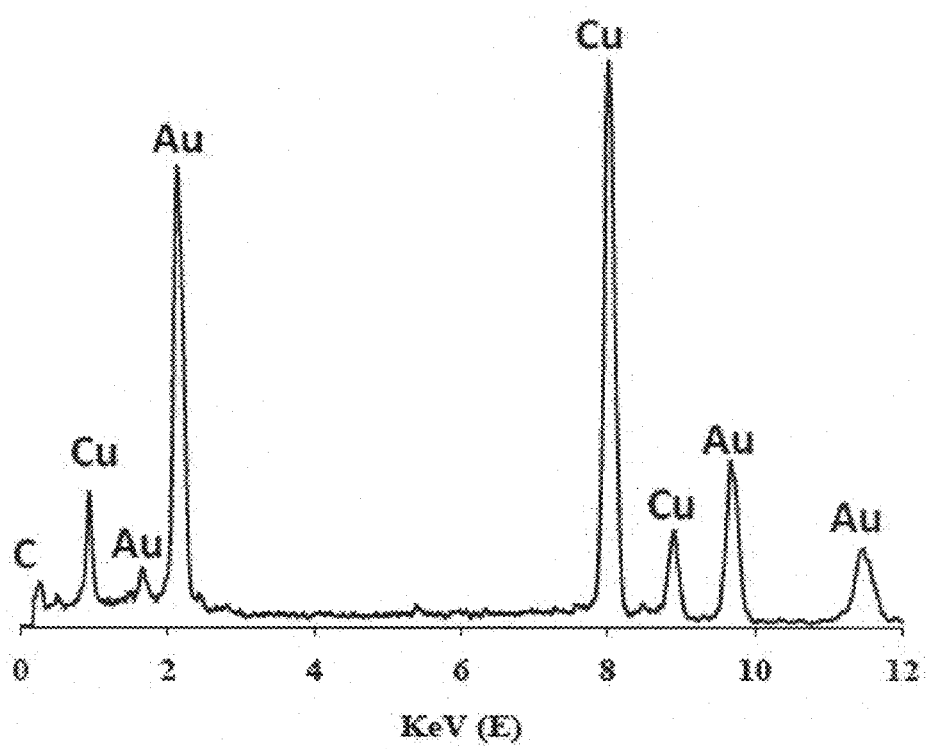
FIG. 2 represents EDS analysis of the synthesized gold nanostructures by Midas-2 (0.2 mg/ml) in deionized water at pH 3 and 37° C.
Figure 3A:
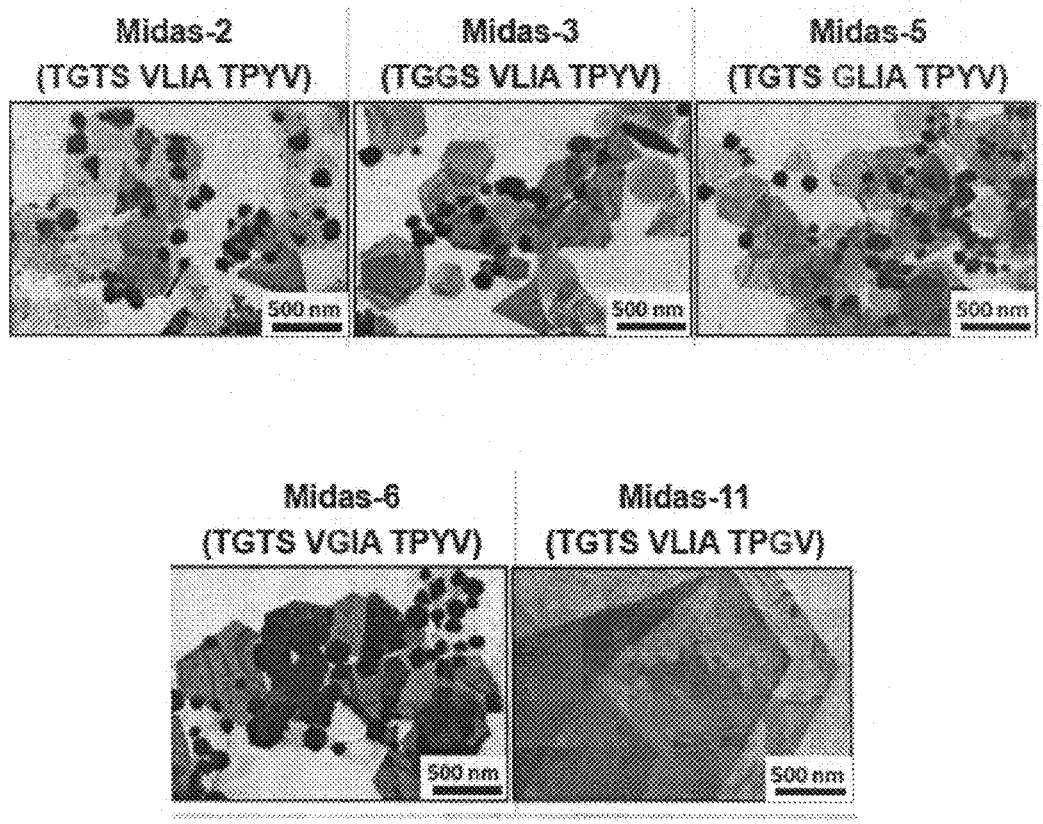
FIG. 3A-3C are TEM images of the synthesized gold nanostructures by peptides Midas-2, 3, 5, 6 and 11 at pH 3 and 37° C. in deionized water (FIG. 3A (a)), UV-Vis spectra of the reaction solutions (FIG. 3B (b)), and amount of the synthesized gold nanostructures by peptides Midas-1 to 12 (FIG. 3C (c)).
Figure 3B:
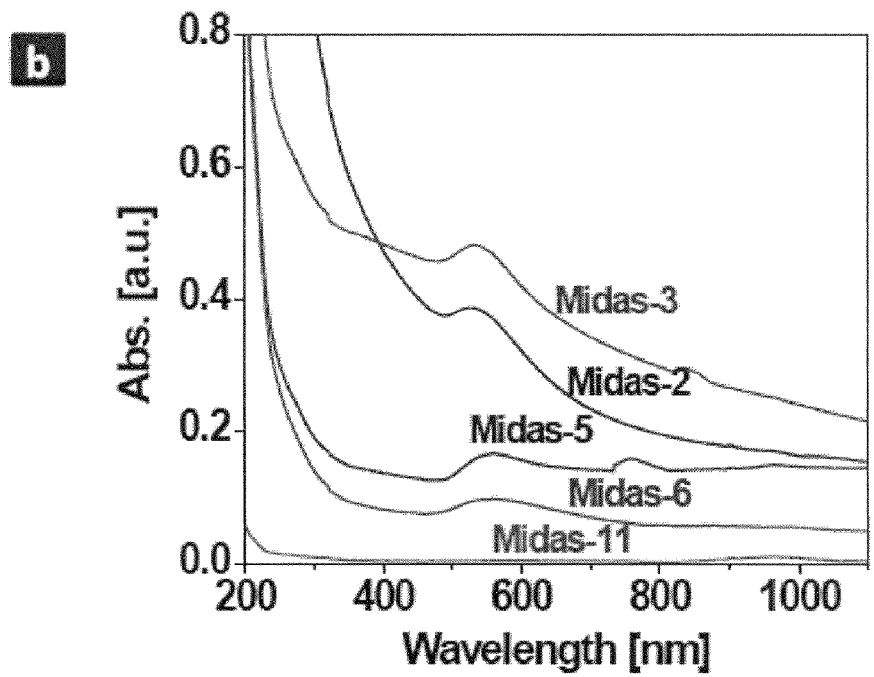
Figure 3C:
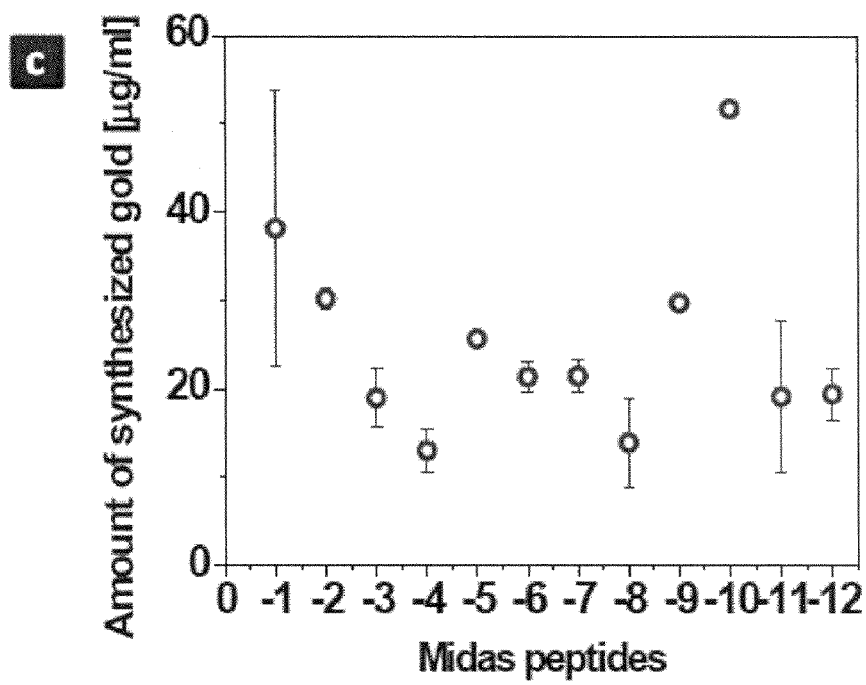

The dodecapeptide Midas-2, which was selected from M13 phage-displayed, combinatorial, peptide libraries, formed monodisperse spherical gold nanoparticles after 3 d of incubation with 0.5 mM HAuCl$_4$ and 0.2 mg Midas-2 peptide in 10 mM phosphate buffer (pH 7.5) at room temperature (FIG. 1A-1C). Gold nanoparticles with average size of 16 nm showed a surface plasmon resonance (SPR) band at around 532 nm with its intense red color (FIG. 2)[16]. It has been known that the SPR peak around 500 nm comes from interacting between gold nanoparticles where the peak position depends on the diameter of nanoparticles[17]. Midas-2 contains a central hydrophobic tetrapeptide (VLIA) flanked by two polar tetrapeptides (TGTS and TPYV) (FIG. 3A-3C). It did not have sulfur- or amine-containing amino acid residues, which was known to bind covalently with the gold particle surface[18], as well as the motif sequences previously found in the gold binding proteins[19]. The pI of Midas-2 was 5.18 which is much lower than other reported gold binding peptides with pI ranges from 8.31 to 8.52[19]. To remove any possible interference of phosphate buffer from reduction reaction of HAuCl$_4$ with Midas-2, the reaction medium was altered to deionized water with initial solution pH of 3.0 at 37° C.

Interestingly, polyhedral, gold nanoparticles, with an average width of ~520 nm, and a small number of trigonal, truncated trigonal, and hexagonal single-crystalline gold platelets, were produced when the Midas-2 peptide was incubated with 0.5 mM HAuCl$_4$ in deionized water (FIGS. 1A (a) and 5A-5C). The formation of metallic gold was confirmed by using x-ray energy dispersive spectroscopy (EDS) and selected area diffraction pattern (SAED) analyses (FIGS. 6A-6C and 4).

Figure 5A:
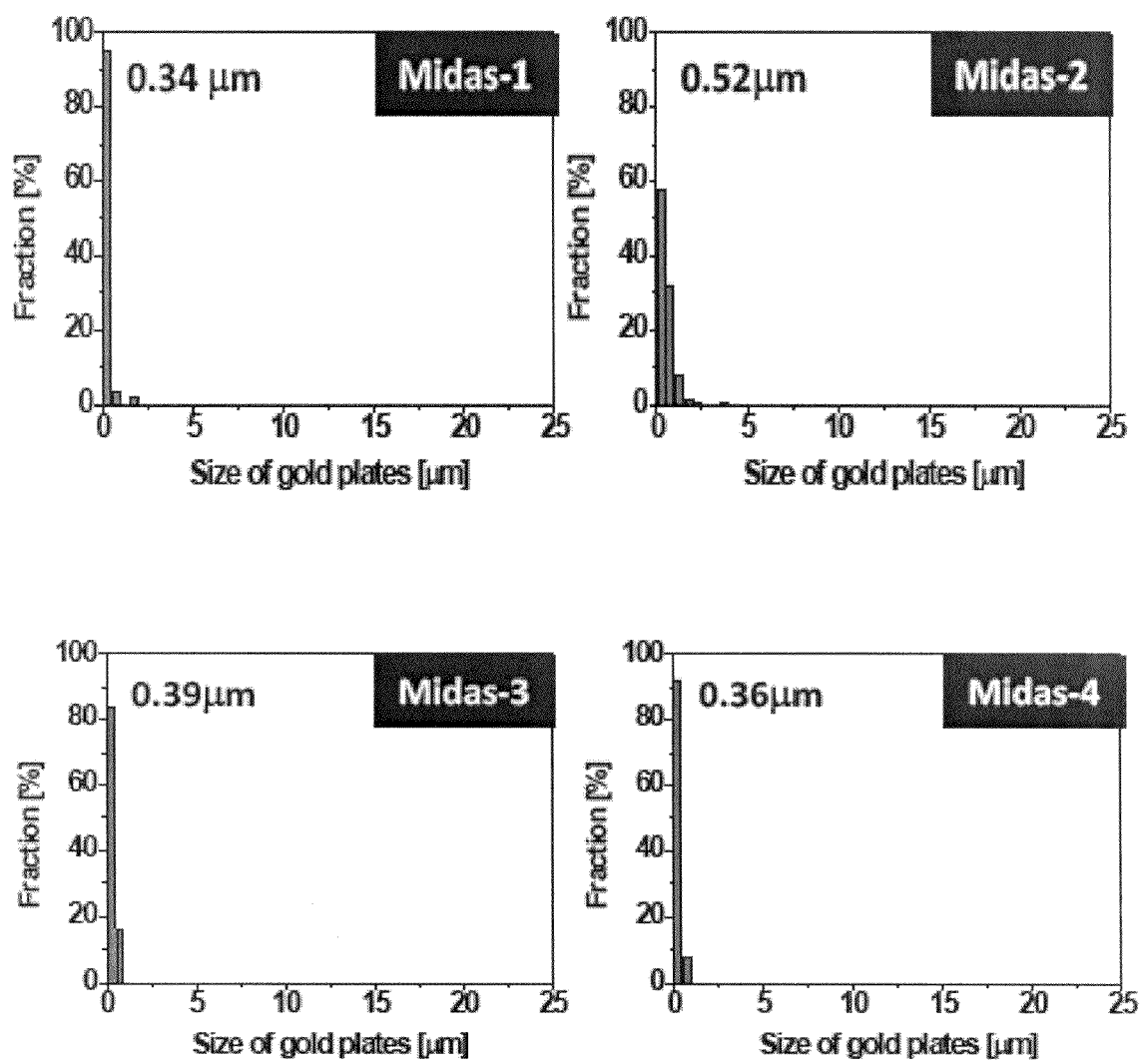
FIG. 5A-5C represent the average size of the synthesized gold nanoplatelets as function of each amino acid substitution with glycine in Midas-2 (0.2 mg/ml) in deionized water at pH 3 and 37° C.
Figure 5B:
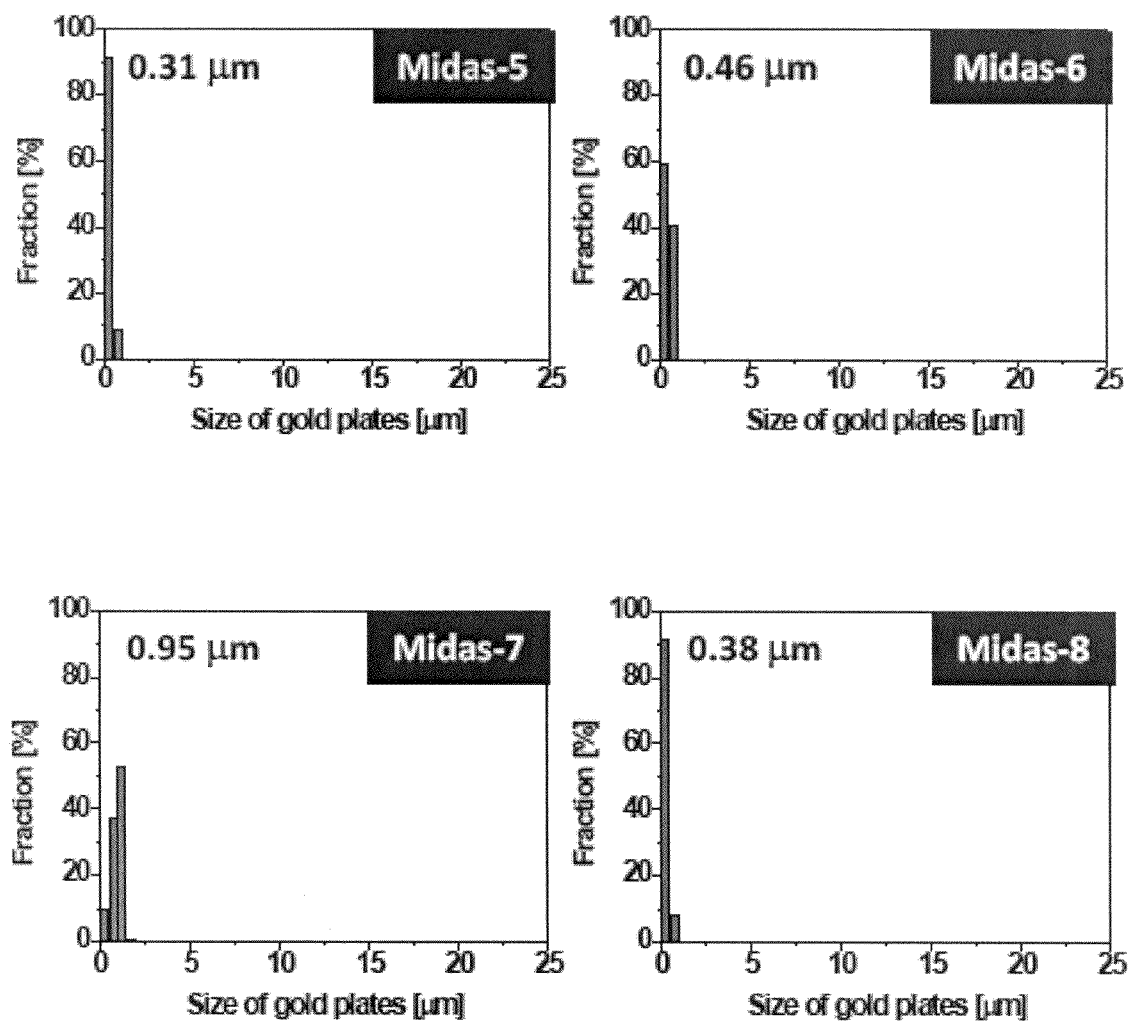
Figure 5C:
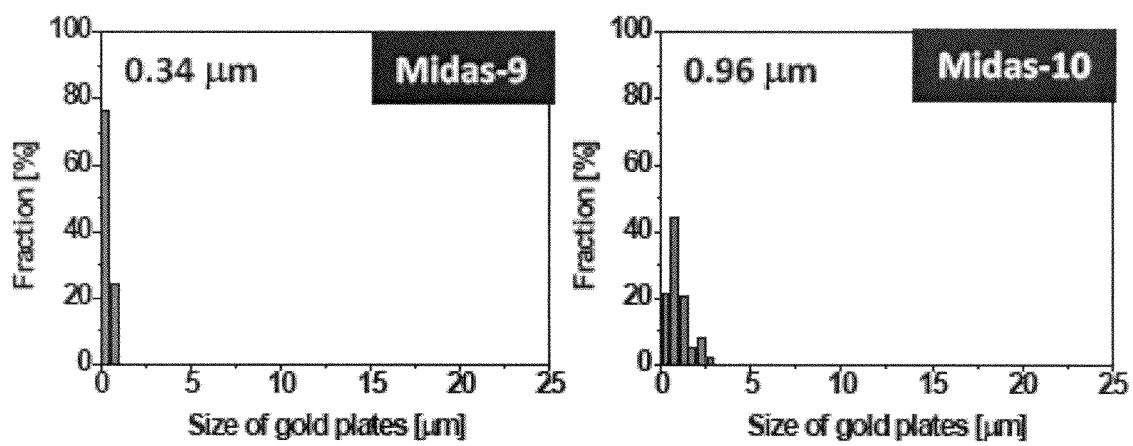
Figure 5C:
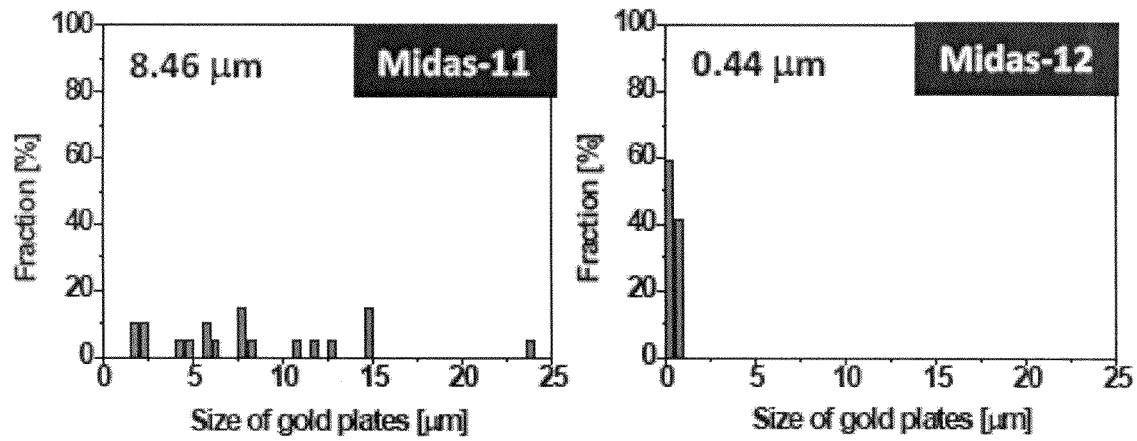
Figure 6A:
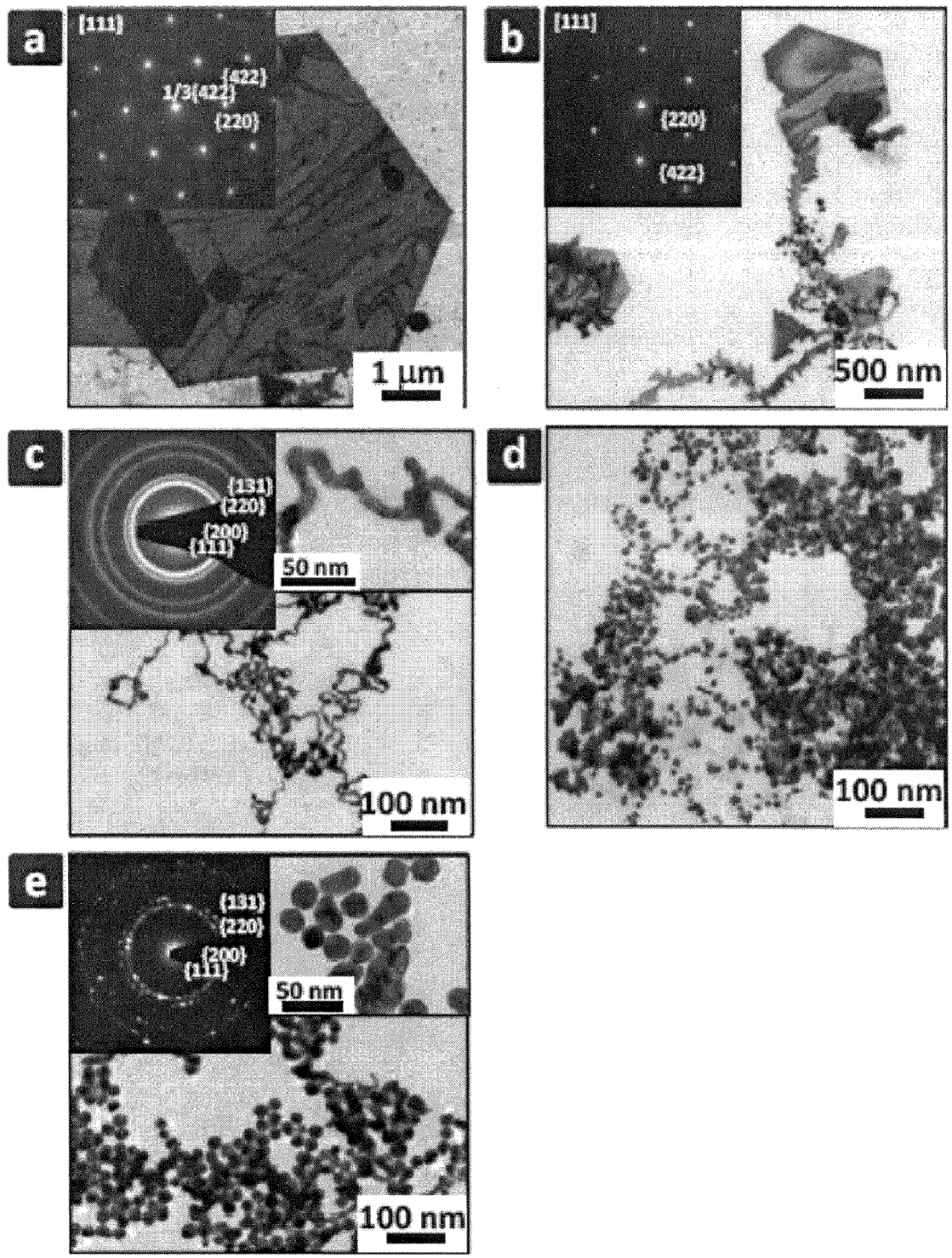
FIG. 6A-6C represent TEM images and SAED patterns (inset) of the synthesized gold nanostructures by peptide Midas-11 with 0.5 mM $HAuCl_4$ at 37° C. and pH 3.0 (FIG. 6A (a)), pH 4.5 (FIG. 6A (b)), pH 5.7 (FIG. 6A (c)), pH 8.1 (FIG. 6A (d)) and pH 9.0 (FIG. 6A (e)). Amount of the synthesized gold based on time (FIG. 6B (g)) and correlation with amount of the synthesized gold and sample solution color (FIG. 6C (f)).
Figure 6B:
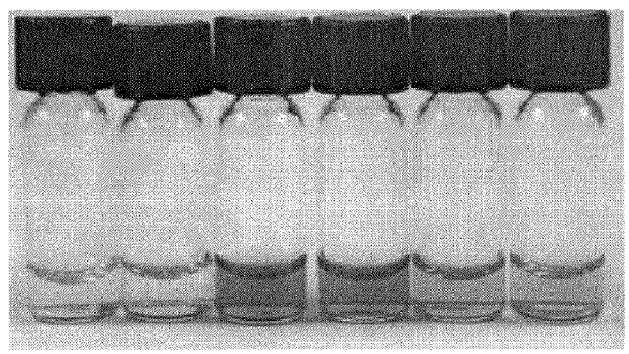
Figure 6C:
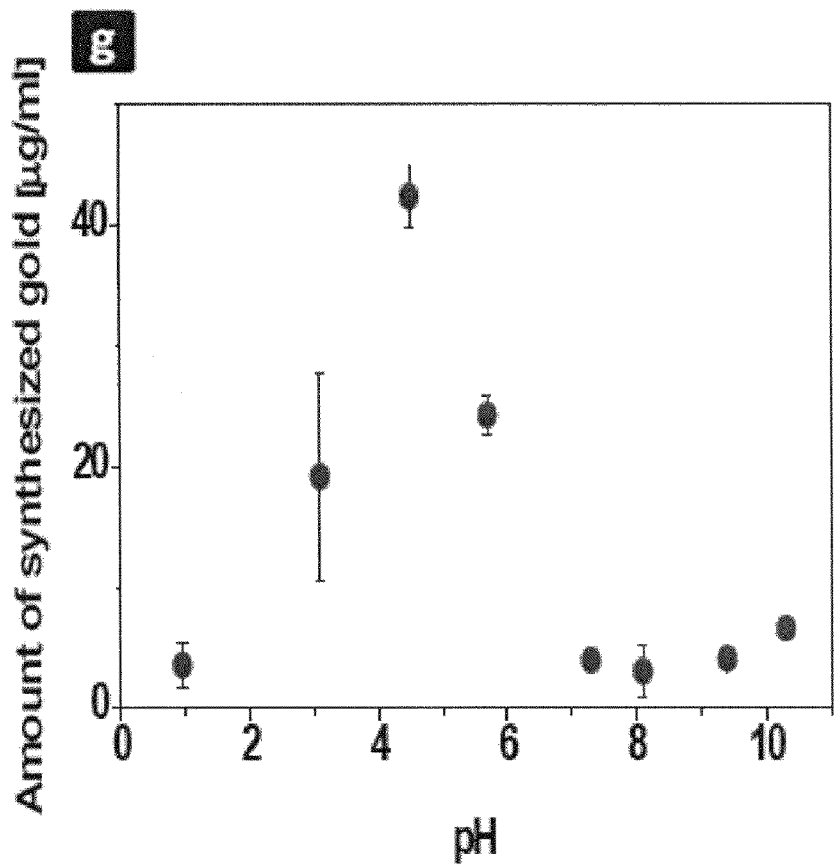
Figure 7:
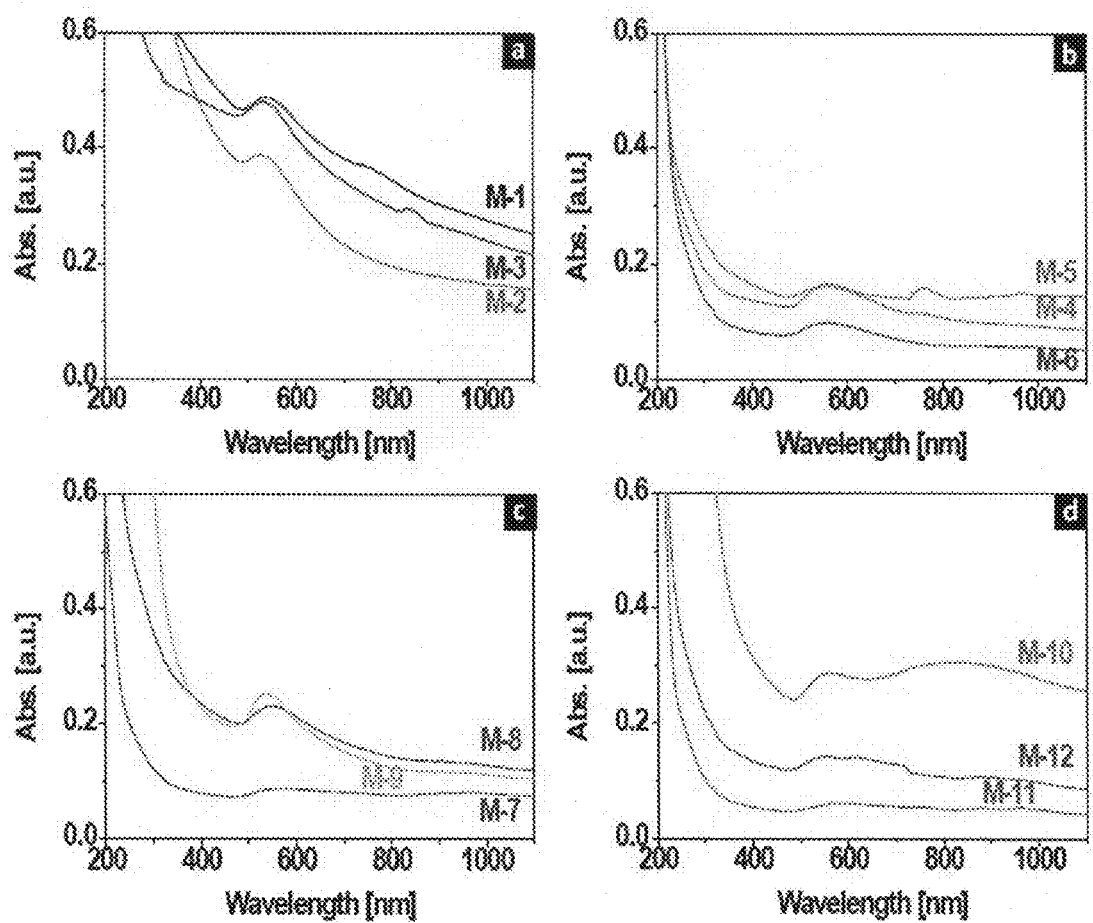
FIG. 7 represents UV-Vis spectra of reaction solutions as function of each amino acid substitution with glycine in Midas-2 (0.2 mg/ml) in deionized water at pH 3 and 37° C.
Figure 8A:
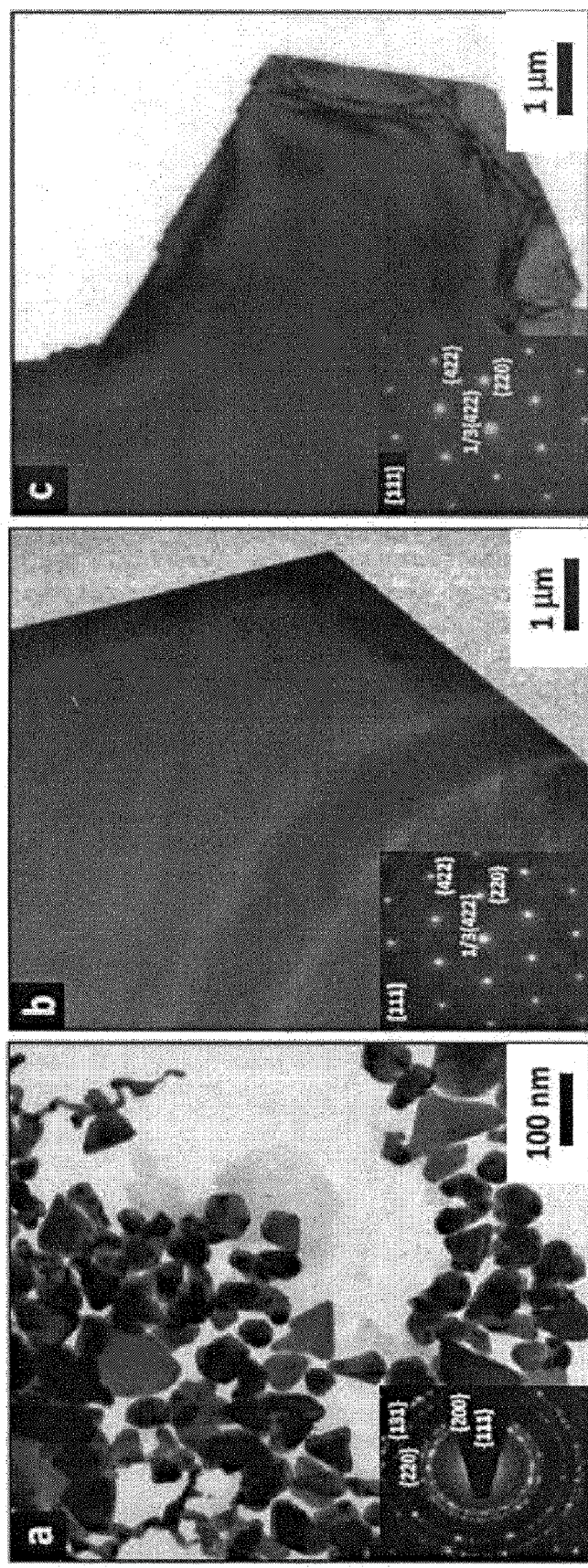
FIG. 8A-8B show TEM images and SAED patterns (inset) of the synthesized gold nanostructures by peptide Midas-11 with 30 mM of $HAuCl_4$ at 37° C. and pH 1.0 (FIG. 8A (a)), pH 3.0 (FIG. 8A (b)), pH 5.0 (FIG. 8A (c)), pH 5.4 (FIG. 8B (d), (e)) and pH 7.0 (FIG. 8B (f)).
Figure 8B:
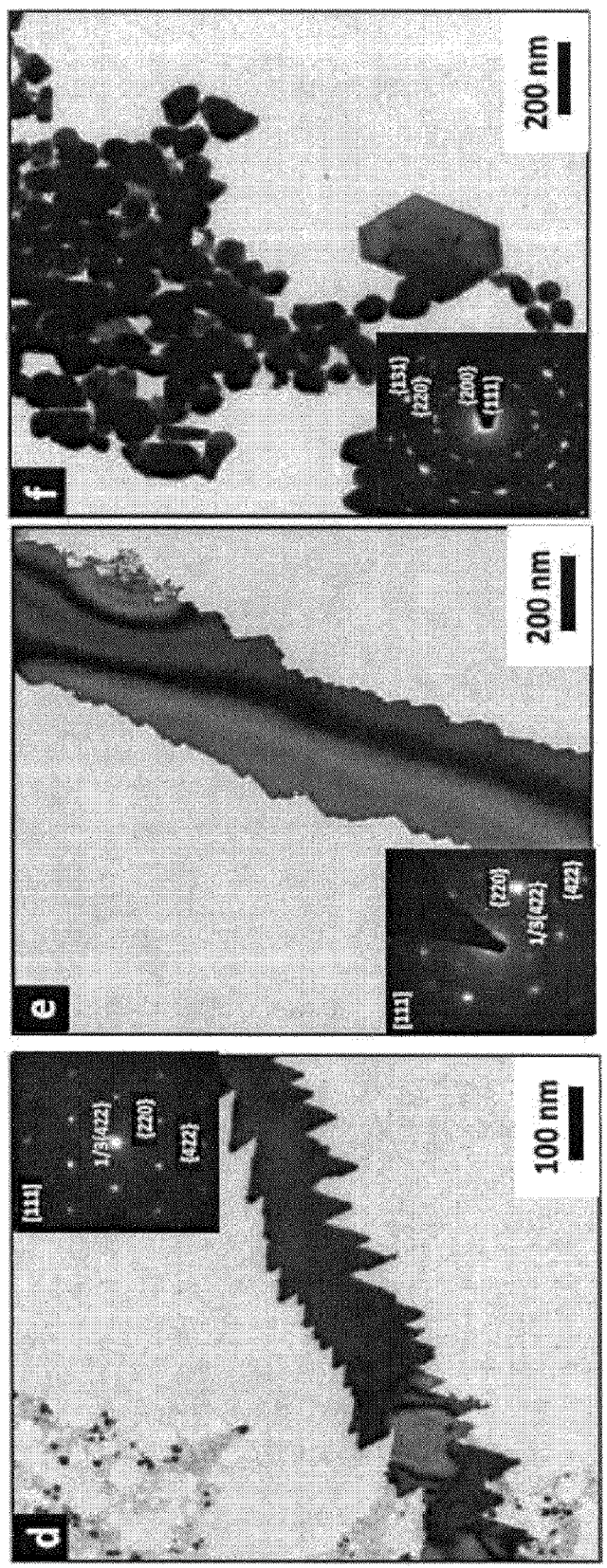
Figure 9:
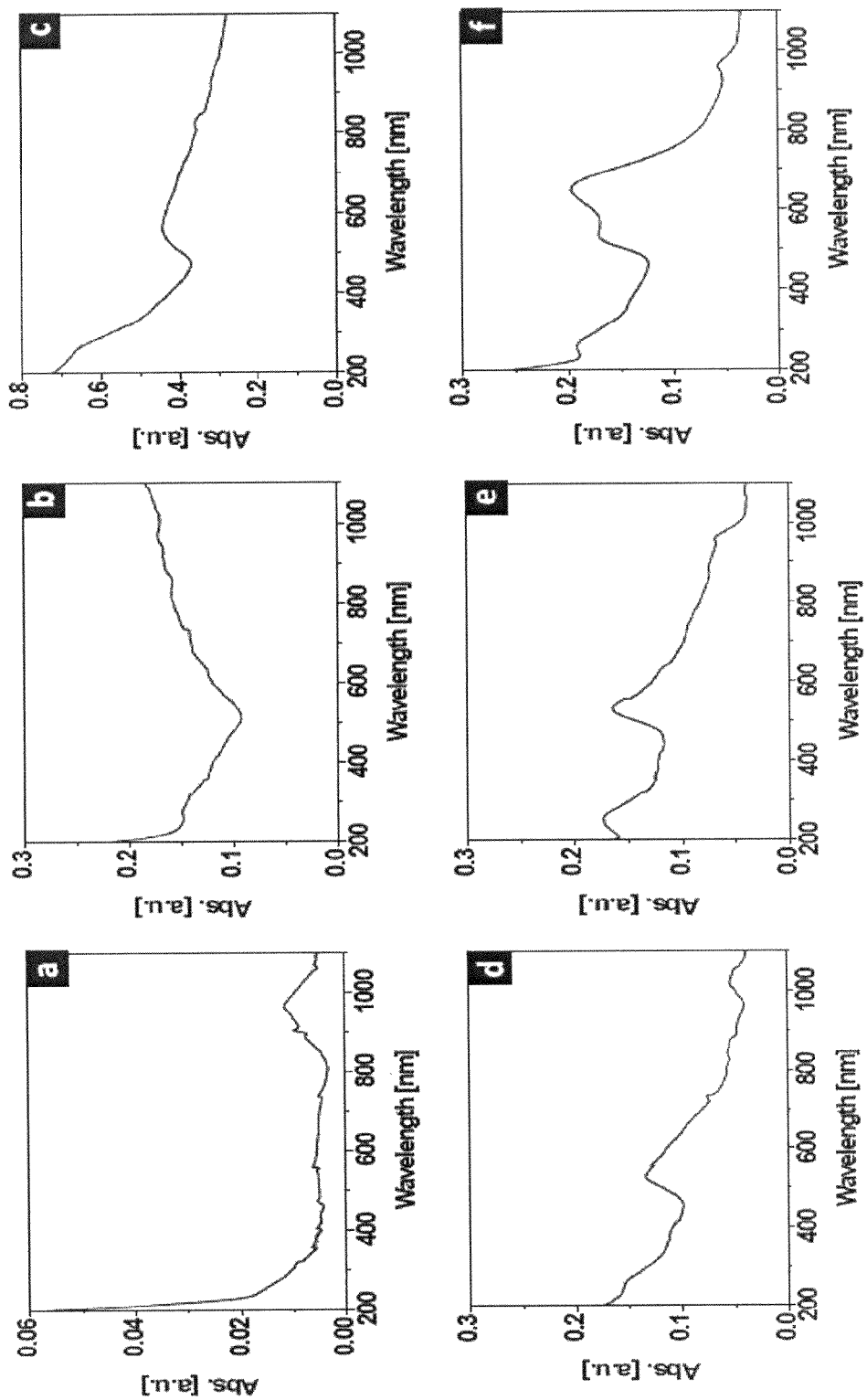
FIG. 9 represents UV-Vis spectra of the reaction solutions containing the synthesized gold nanostructures by peptide Midas-11 with 0.5 mM HAuCl$_4$ at 37° C. in deionized water with different pH conditions, pH 3.1 (a), pH 4.5 (b), pH 5.7 (c), pH 8.1(d), pH 9.4 (e) and 10.3 (f).

To determine how the primary sequence of the Midas-2 peptide influenced the formation of gold nanostructures, each amino acid in Midas-2 was individually substituted with glycine, producing a set of 12 different mutated Midas peptides (FIGS. 3A-3C and 4). As expected, the calculated pI values of the majority of substituted peptides remained at 5.18, except for Midas-1 and Midas-11 with pIs of 5.52 and 5.19, respectively. Surprisingly, when incubated at pH 3 at 37° C. with 0.5 mM HAuCl$_4$, the peptide Midas-11, in which the tyrosine at the $11^{th}$ position was replaced with glycine, produced a few large trigonal, truncated trigonal, and hexagonal gold platelets with widths of ~24 μm and heights of 30-150 nm. Under the same reaction conditions, the rest of the mutated Midas peptides produced a mixture of trigonal, truncated trigonal, and hexagonal gold platelets and polygonal gold nanoparticles with variable sizes and shapes (FIGS. 1A-1C and 4), ranging from submicron to a few micrometers in size (FIG. 5A-5C).

Due to the different sizes and shapes of the gold nanostructures, the reaction solutions showed different SPR band patterns. For example, the SPR band at 520-580 nm was significantly reduced as the ratio of platelets to nanoparticles increased. No significant SPR band was observed in the gold nanostructures produced by Midas-11 (FIGS. 3B (b) and 7). The substitution of each amino acid in the Midas-2 peptide with glycine also resulted in a reduction in the concentration of gold ion in the reaction solution. Moreover, substitution of the N-terminal amino acid threonine and the conformationally-rigid amino acid proline with glycine, present in peptides Midas-1 and Midas-10, respectively, produced a substantially greater amount of gold nanostructures after 3 days of incubation than did the remainder of the tested Midas peptides (FIG. 3C (c)).

The influence of solution pH and $HAuCl_4$ concentration on the formation of gold nanostructures by Midas-11 was investigated. The various gold structures synthesized by Midas-11 at different pH are shown in FIGS. 6A-6C and 8A-8B, where the concentration of $HAuCl_4$ was fixed at 0.5 and 30 mM, respectively. Both the solution pH and gold concentration had a dramatic influence on the shapes and sizes of gold nanostructures synthesized by Midas-11. The nanostructures produced were polycrystalline polyhedral gold nanoparticles (FIG. 6A (d)), peanut-shaped aggregates (FIG. 6A (e)), large hexagonal or trigonal shape platelets (FIGS. 6A (a), 8A (b) and 10) from ~10 to ~100 microns in width, or long single crystalline nano-fibers or extended long single crystal nanoribbons consisting of trigonal segments joint together at the vertices and sides (FIG. 6A (b), and 8A (c), 8A (d)-(e)). In addition, incubation of Midas-11 with 0.5 mM $HAuCl_4$ at 37° C. and pH 5.7 resulted in the formation of a two-dimensional network structure of gold nanowires with widths of 10-20 nm in size (FIG. 6A (b)). The variation in the size and shape of the nanostructures produced was not random and was directly controlled by the experimental parameters tested.

Taken together, results of these studies indicated that solution pH had a profound effect on the shape of gold crystals synthesized by the Midas-11 peptide. At pH>7 and with 0.5 mM $HAuCl_4$, Midas-11 formed random aggregates of small isometric gold nanoparticles ranging from 5 to 20 nm in diameter with single or double narrow SPR peaks between 500 and 600 nm and pink or purple colored solutions (FIGS. 6B (f) and 9). In contrast, at pH ~5 and with concentrations of $HAuCl_4$ ranging from 0.5 to 30 mM, the Midas-11 peptide formed extended gold nanoribbons consisting of trigonal segments (FIG. 8B (d)) and large trigonal or hexagonal platelets crystals at the one end of the ribbon (FIGS. 6A (b) and 8A (c)). Selected area diffraction patterns (SAED) of these "kite-shaped" ribbons indicated that entire structures were composed of single crystals mixed with isolated trigonal or hexagonal platelets crystals. The "kite-shape" ribbons were elongated parallel to the <211> direction and the sides of the trigonal or hexagonal facets were parallel to the {111}-type faces. The ribbons formed, with 30 mM $HAuCl_4$ were tens of microns in length and had widths ranging from 100 nm to 3 μm (FIGS. 8B (d), 8B (e) and 11). The hexagonal or trigonal platelets formed were also relatively large, with sides ranging from hundreds of nanometers to tens of microns. The UV-Vis spectra of the reaction solution, at $HAuCl_4$ concentration of 0.5 mM, showed broad absorption over the 500 nm range, which was attributed to the anisotropic gold nanowires and ribbon structures produced (FIGS. 6A (b) and 6A (c))[20]. The color of solution was grey to dark purple (FIGS. 6B (f) and 9).

Figure 10:
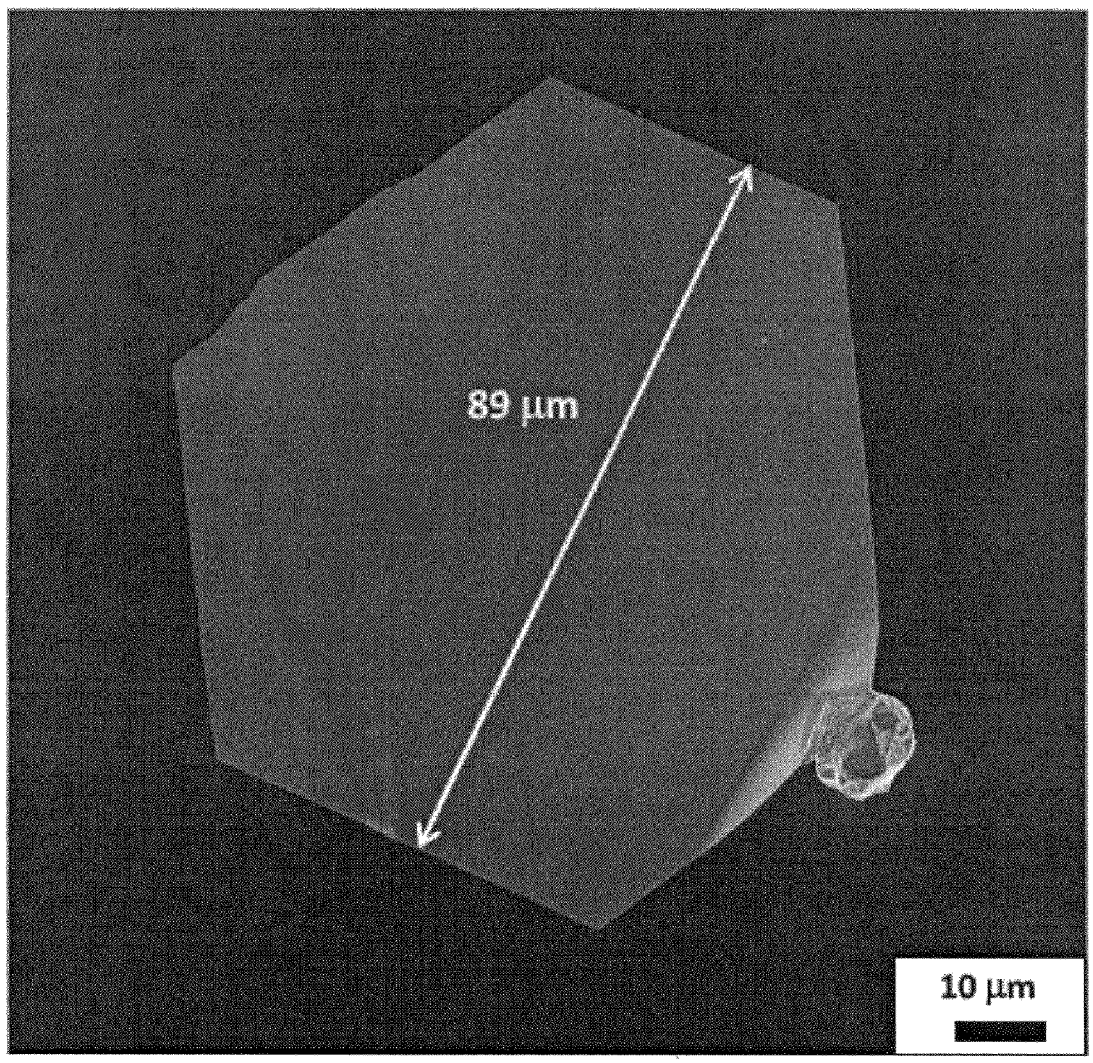
FIG. 10 shows SEM images of the largest gold nanoplates synthesized in 3 days by peptide Midas-11 with 30 mM of HAuCl$_4$ at pH 1.7 and 37° C.
Figure 11:
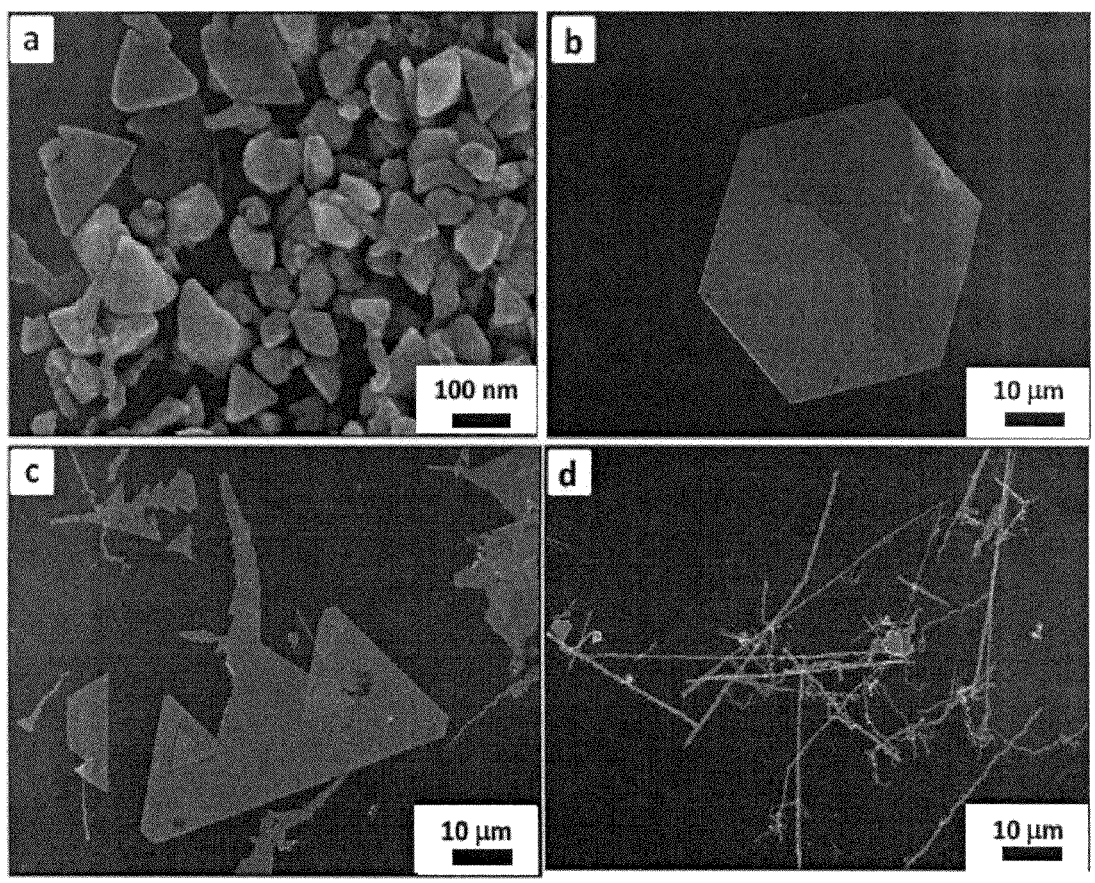
FIG. 11 represents SEM images of the synthesized gold nanostructures by peptide Midas-11 with 30 mM of HAuCl$_4$ at 37° C. and pH 1.0 (a), pH 3.0 (b), pH 5.0 (c), and pH 5.4 (d).
Figure 12A:
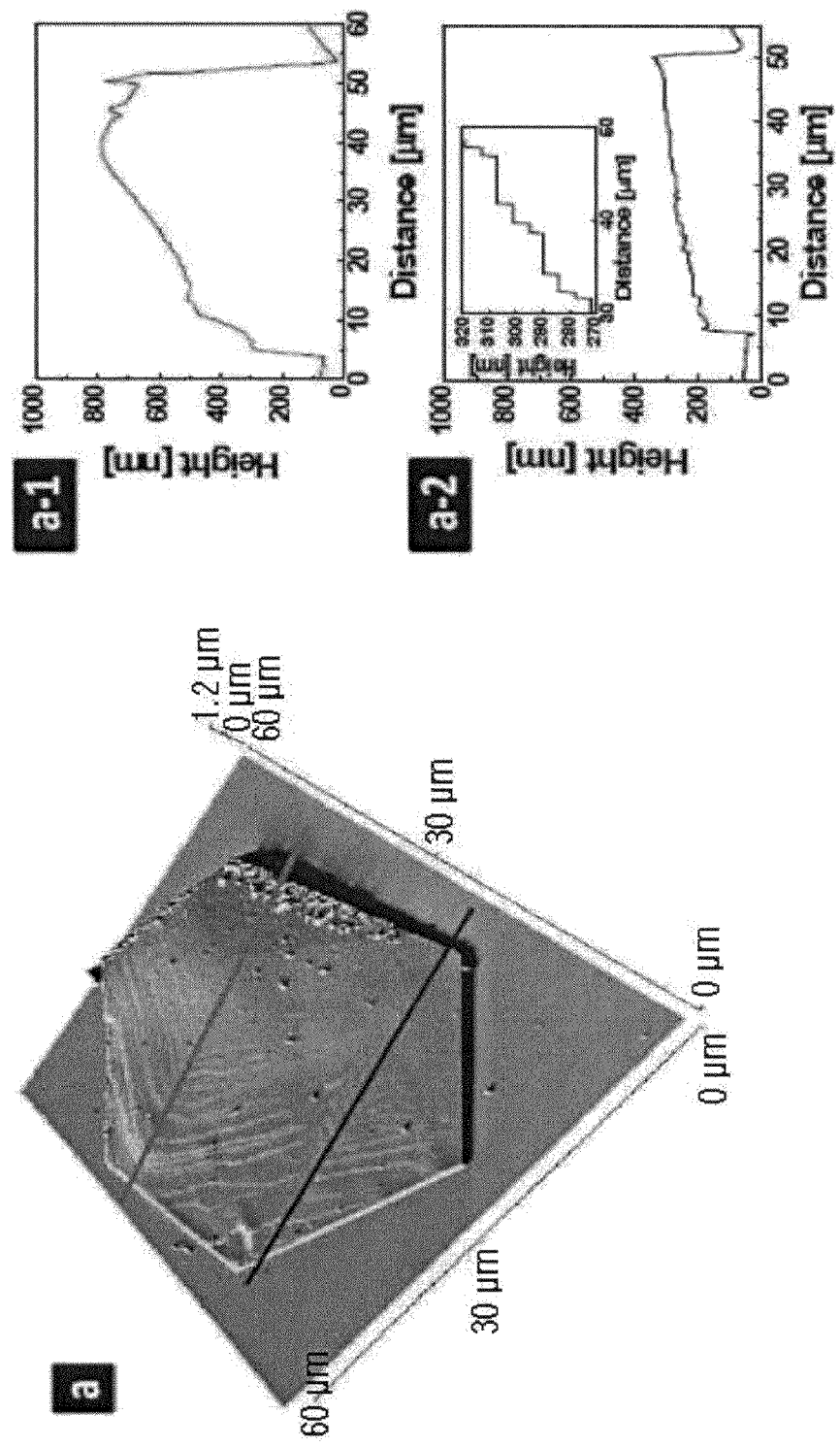
FIG. 12A-12C represent AFM images of the synthesized gold nanostructures with 30 mM HAuCl$_4$ at pH 3.0 (FIG. 12A (a)), pH 5.0 (FIG. 12B (b)) and pH 5.4 (FIG. 12C (c)) at 37° C. and thickness profiles; (a-1 and -2) for (FIG. 12A (a)), (b-1) for (FIG. 12B (b)), and (c-1) for (FIG. 12C (c)).
Figure 12B:
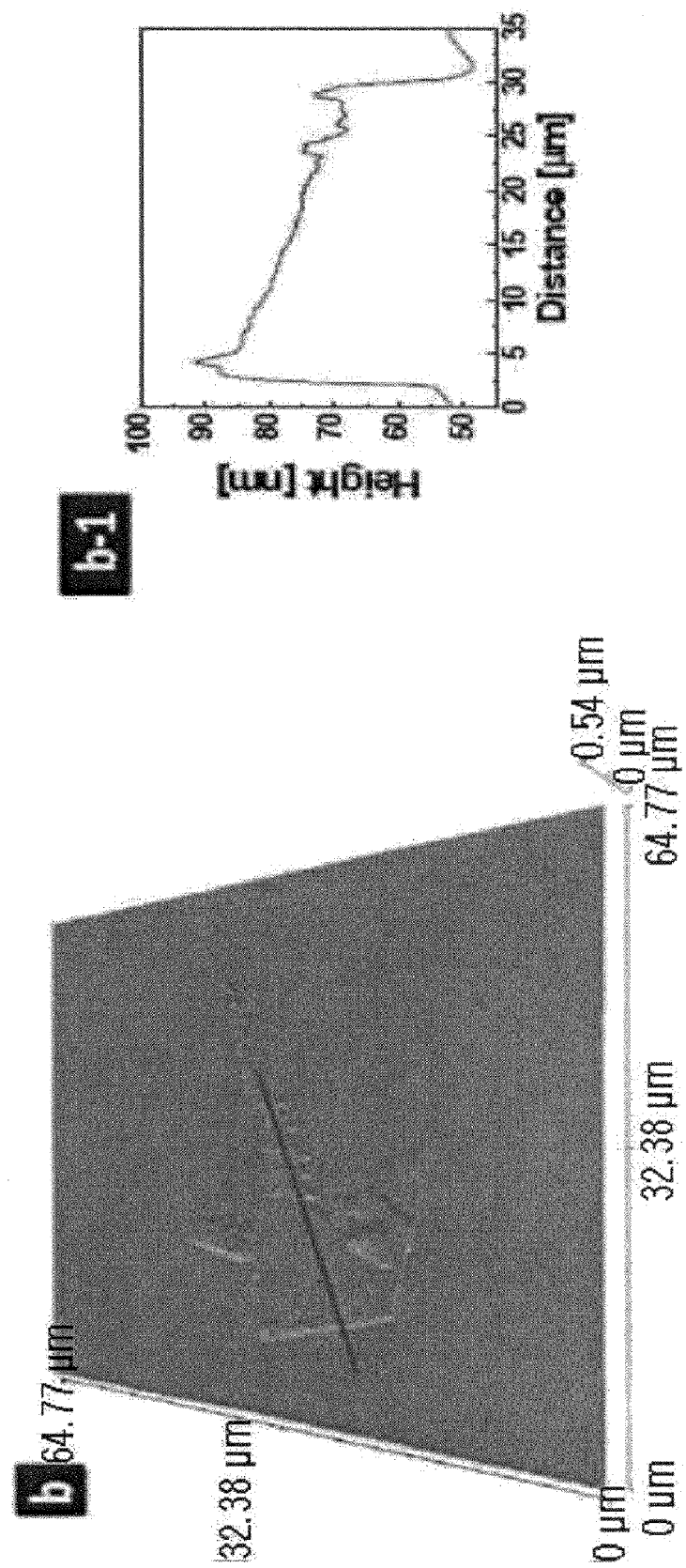
Figure 12C:
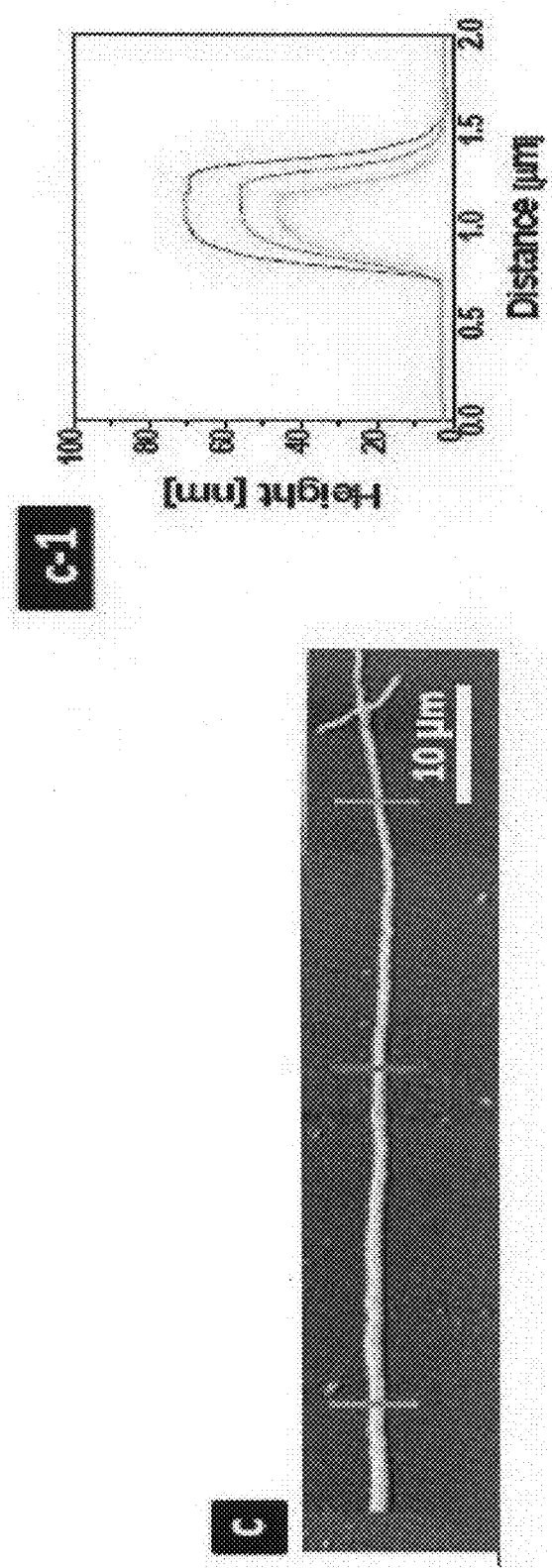

At pH≦3, Midas-11 formed large, nanometer thick gold platelets with hexagonal or trigonal shapes. The width of the platelets varied from several microns to ~100 microns at $HAuCl_4$ concentrations of 0.5 mM and 30 mM. The width of the platelets was controllable by adjusting gold ion concentration, a maximum width of 89 μm was observed with 30 mM $HAuCl_4$ at pH 1.7 (FIG. 10). The trigonal and hexagonal platelet crystals which were produced with Midas-11 in 30 mM $HAuCl_4$ at pH 3 had well-developed extended flat {111}-type faces, with minor growth steps. The terrace-like steps are normally formed during spiral growth. Analysis of the surface of hexagonal platelets using atomic force microscopy (AFM) indicated that the crystal was likely formed from spiral growth with screw dislocation (FIG. 12A (a)). The sides of the trigonal or hexagonal plates were defined by {211}-type faces, and the vertices of the trigons or hexagons were along the <110>-type direction. The SAED patterns along the [111]-zone axis of the platelets, which was normal to the extended flat faces, showed superstructure reflections at 2.5 Å due to twinning on the (111)-type planes. Twinning of large and small trigonal and hexagonal platelets has previously been reported[21]. In general, three mechanisms have been proposed to explain the growth of gold particles specifically for anisometric crystals and aggregates[22], including (i) capping agent, (ii) surfactant, and (iii) kinetics and thermodynamic controlled effects. The development of distinctly different crystal shapes and sizes in the experiments done using the Midas-11 peptide and varying solution pHs suggested that the kinetics of nucleation and growth likely controlled the final shape and size of the gold particles. Our hypothesis could be supported by time dependent studies (Please see supplemental materials).

Figure 13:
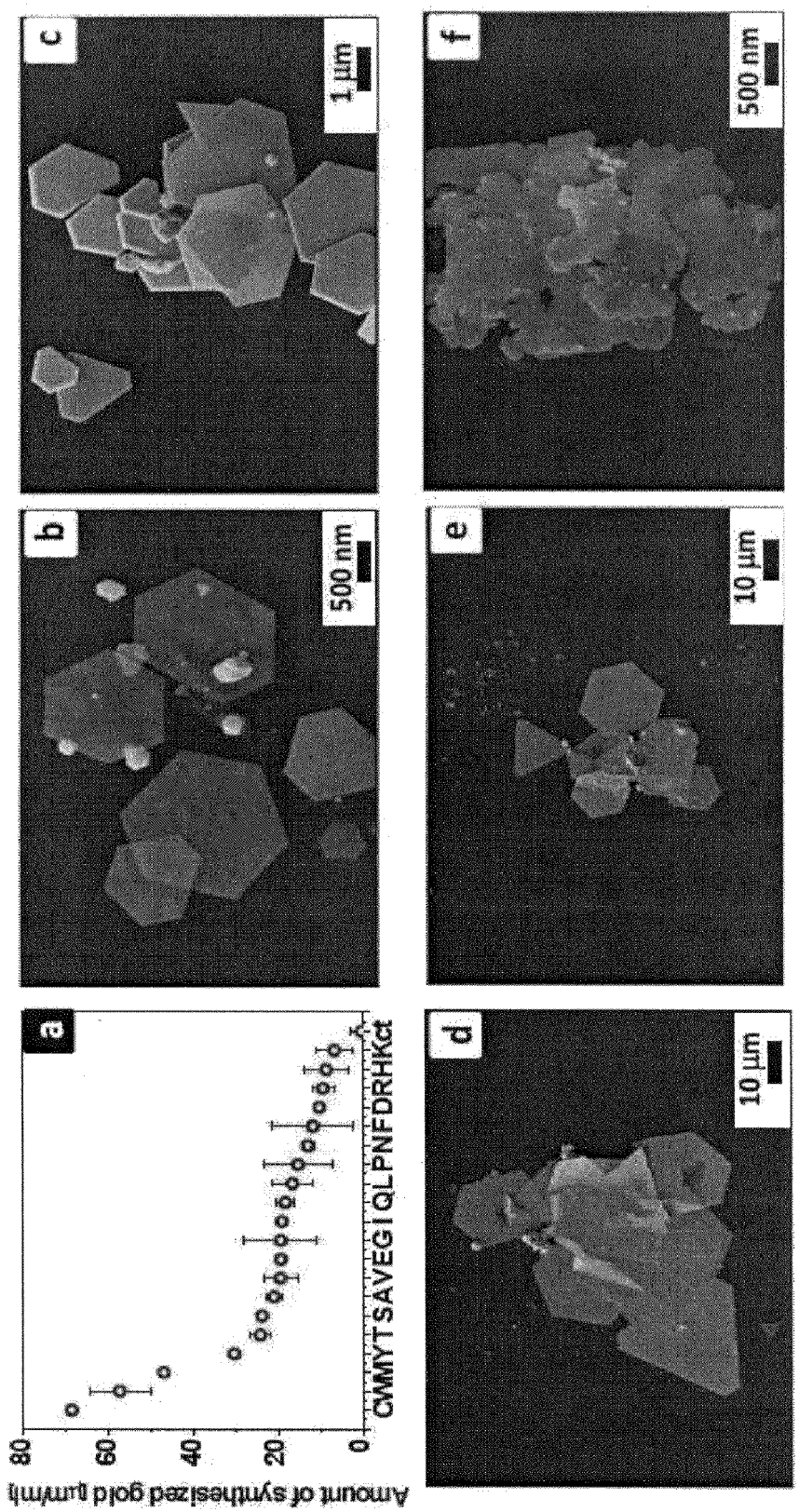
FIG. 13 represents amount of the synthesized gold nanostructures by 20 different peptides Midas-11$_A$ to $_Y$ (SEQ ID NO: 31) (a) and representative SEM images of gold nanostructures by peptides Midas-11C (b), Midas-11$_S$ (c), Midas-11$_I$ (d), Midas-11$_D$ (e) and Midas-11$_R$ (0 at pH 3 and 37° C. in deionized water.

Since the Midas-11 peptide produced exceptionally nanometer-thick, large, gold platelets at pH of 3 relative to the other Midas peptides, we also examined the influence of 19 other amino acids (termed Midas-$11_{Amino\ Acid}$) at the $11^{th}$ position of Midas-11, for the formation of gold structures and reduction amount of $HAuCl_4$ in the reaction solutions. After replacement, the pI values of the Midas-$11_{H,K,\ and\ R}$ increased noticeably to 6.40, 8.41, and 9.41, respectively, compared to a pI 5.19 for Midas 11. In contrast, the calculated pI values of Midas-$11_{D\ and\ E}$ decreased to 3.8 and 4.0, respectively. Based on results obtained from the reaction of $HAuCl_4$ with the modified peptides at pH 3 and 37° C. (FIG. 13), the general rules controlling sizes of gold nanostructures by the Midas-$11_{Amino\ Acids}$ could be deduced as follows: 1) Midas-11 containing substitution of the $11^{th}$ glycine with cysteine, tryptophan, or methionine amino acids that were previously shown to bind to metallic gold[23], produced substantially greater amounts (46-68 μg) of gold in the reaction solutions than did the other amino acids. These peptides formed trigonal, truncated trigonal, and hexagonal gold platelets ≦1-2 μm in size, as well as small amounts of irregular polygonal gold nanoparticles (FIGS. 13(b), 16A-16C and 17A-17E). 2) In contrast, Midas-$11_{Y,T\ and\ S}$ formed gold platelets in the range of 0.5 to 10 μm (FIGS. 13(c), 16A-16C and 17A-17E), whereas Midas-$11_{A,V,E,R,Q,L,P,G,N,F,\ and\ D}$ (FIGS. 13(d), 13(e) and 16A-16C) formed gold platelets in the 10 μm size class, and deposited 20 to 10 μg of gold in the reaction solutions (FIG. 17A-17E). 3) Substitution of the $11^{th}$ glycine in the Midas-11 peptide with the polar, basic, amino acids, histidine, lysine, or arginine, caused to pI to increase to 6.40, 8.41, and 9.41, respectively. These substitutions produced relatively lower quantities of gold than did the other amino acids, and resulted in formation of irregular shaped and uncontrolled sizes of gold platelet-like structures (FIGS. 13(f) and 16A-16C).

Figure 19:
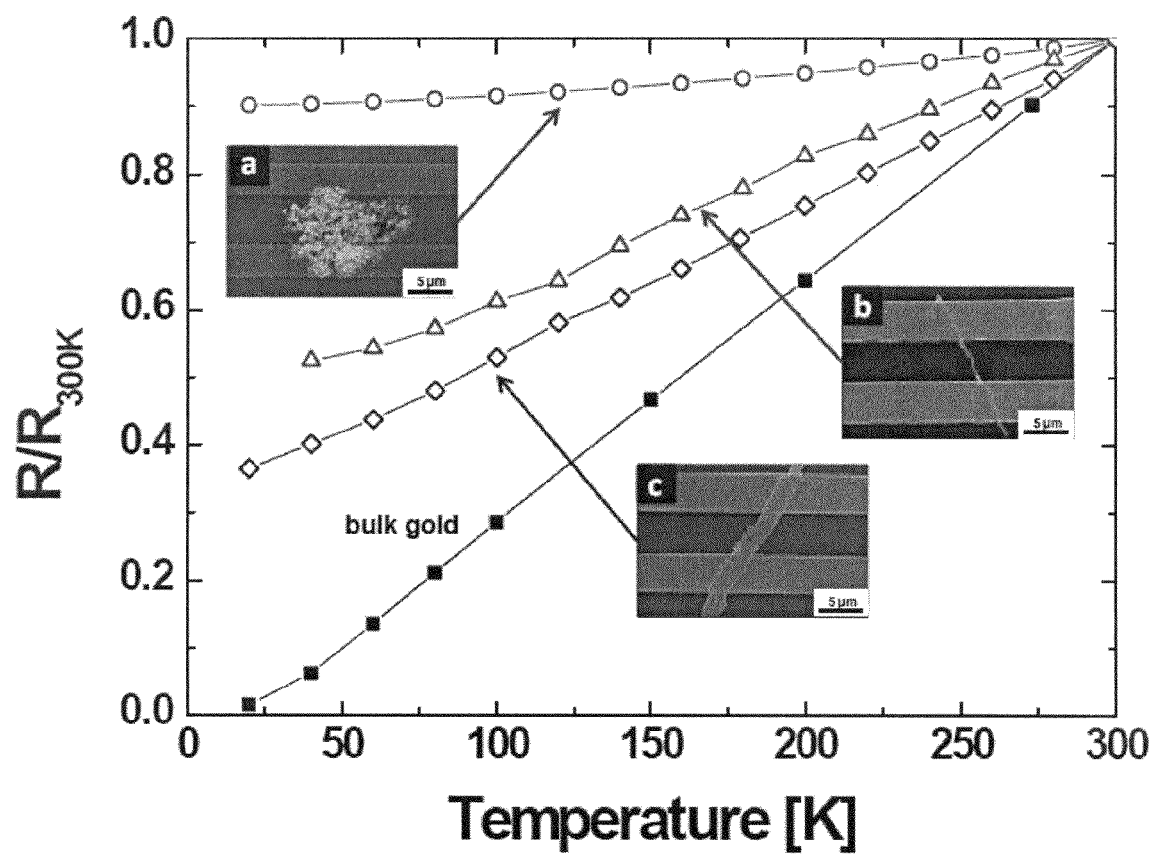
FIG. 19 represents temperature dependence of resistance normalized to the resistance at 300 K for the synthesized gold nanostructures by peptide Midas-11 at 37° C. and pH 5.7 with 0.5 mM HAuCl$_4$ (a), and at 37° C. and pH 5.4 with 30 mM of HAuCl$_4$ (b and c).

To apply as an interconnector for nanoelectronics and a transducer for nano gas sensor (e.g. $H_2S$ sensor), the electrical properties must be characterized. The temperature dependence of electrical resistance of the synthesized gold nanostructures, including nanowire bundles and single nanoribbons of different widths, was measured using two point electrical contacts. The gold nanostructures were assembled on pre-fabricated interdigitated 5 μm gap gold electrodes using the AC dielectrophoretic alignment method. The peak-to-peak AC voltage was 1 V and the frequency was fixed at 100 kHz. As shown in FIG. 19, the temperature dependent electrical resistance normalized to the resistance at 300 K of the gold nanostructures (i.e. the temperature coefficient of resistance (TCR, α)) decreased as the dimension of nanostructures decreased, indicating that lattice imperfection including material surface becomes a dominant factor causing the reduction of α. In addition, the electrical resistivity of gold nanoribbon (approximately 10-40 μohm cm) was one order of magnitude greater than bulk gold (2.27 μohm cm). These data indicated that detailed studies are needed to understand the electron transport at nanoscale where surface phenomena become a dominant factor governing the properties of materials.

In conclusion, single amino acid change of dodecapeptide, Midas-2, selected from phage-displayed combinatorial peptide libraries, which acted as both reducing and capping agents, can control the size and shape of gold nanostructures. In addition, peptide-mediated size and shape control of gold structures can be extensively affected with change of reaction conditions including pH and concentration of $HAuCl_4$ results in diverse size (from a few nanometer to close to one hundred micron) and shape (i.e. nanoparticles including peanut-like shapes, nanowires, nanoribbons, kite and tail structures, and nanometer thick platelets) of gold nanostructures. Therefore, synergistic effects of peptide structure and reaction conditions on modulating synthesis of gold structures can provide crucial tools architecting the next generation nanodevices.

Supplemental Materials

In alkaline conditions at pH above 7, the gold particles develop fine nanometer-size crystals and aggregates, suggesting that the nucleation rate is high but subsequent growth rate is strongly reduced and particles do not grow significantly beyond their original nucleation size.

Figure 14:
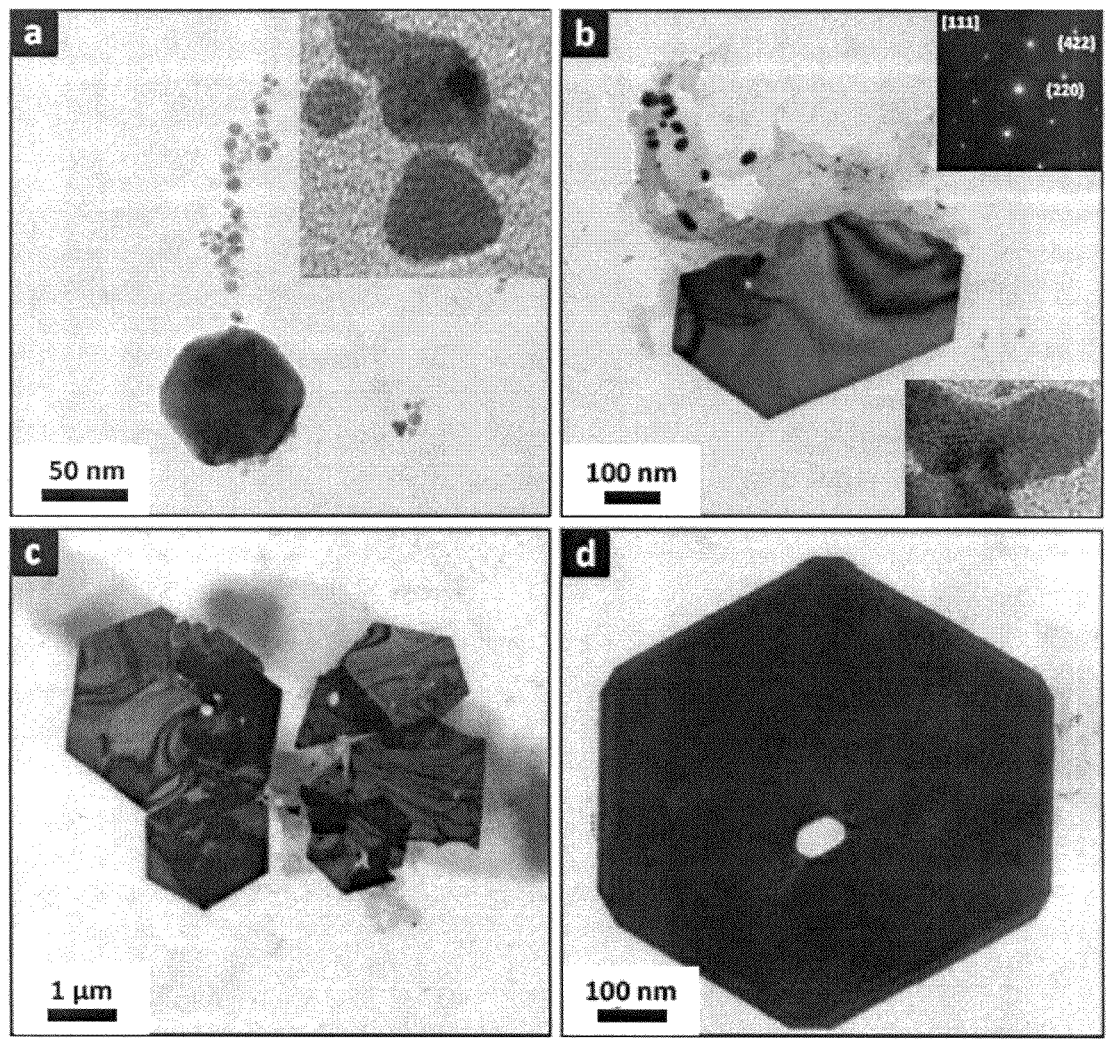
FIG. 14 shows TEM images of the synthesized gold nanostructures by Midas-11 with 0.5 mM HAuCl$_4$ at pH 3 in different incubation time of 6 hrs (a), 24 hrs (b and c), 72 hrs (d). SAED pattern insets from the gold nanoplatelet.
Figure 15:
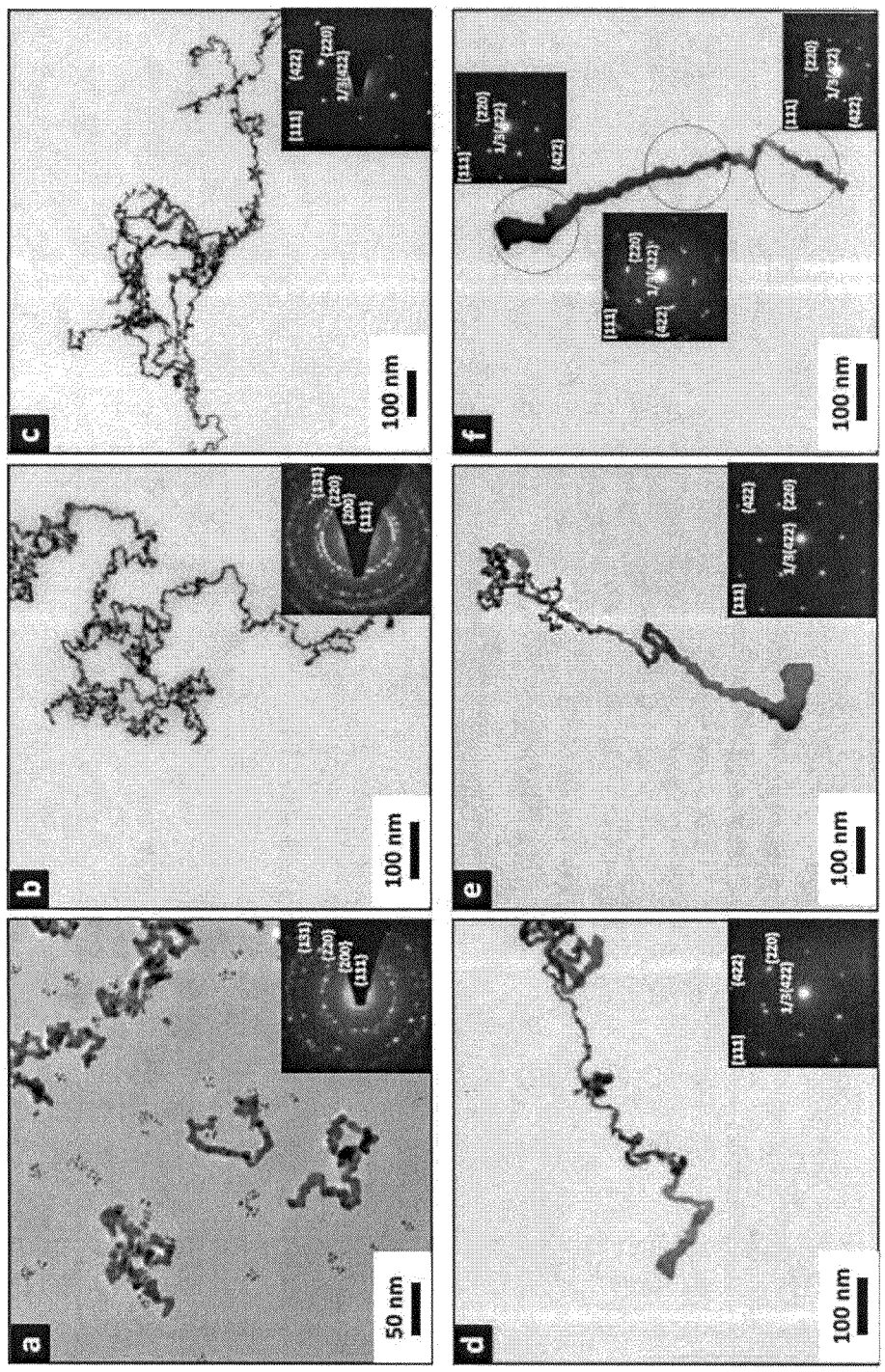
FIG. 15 represents TEM images of the synthesized gold ribbon-like nanostructures by Midas-11 with 0.5 mM HAuCl$_4$ at pH 4.5 in different incubation time of 6 hrs (a), 12 hrs (b), 24 hrs (c), 48 hrs (d), and 72 hrs (e and f). SAED pattern insets from the ribbon-like nanostructures.
Figure 16A:
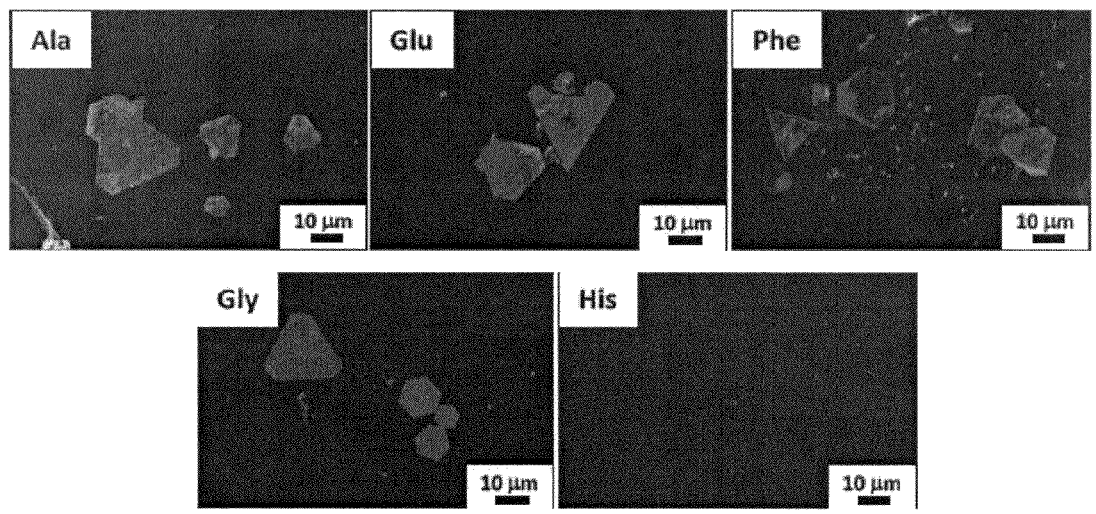
FIG. 16A-16C represent SEM images of the synthesized gold nanostructures by 20 peptides Midas-11$_A$ to $_Y$ (except Midas-11$_{C,S,I,D}$ and $_R$ described in FIG. 13 in the manuscript) substituted by 20 amino acids on the 11th position of Midas-11 (0.2 mg/ml) in deionized water at pH 3 and 37° C.
Figure 16B:
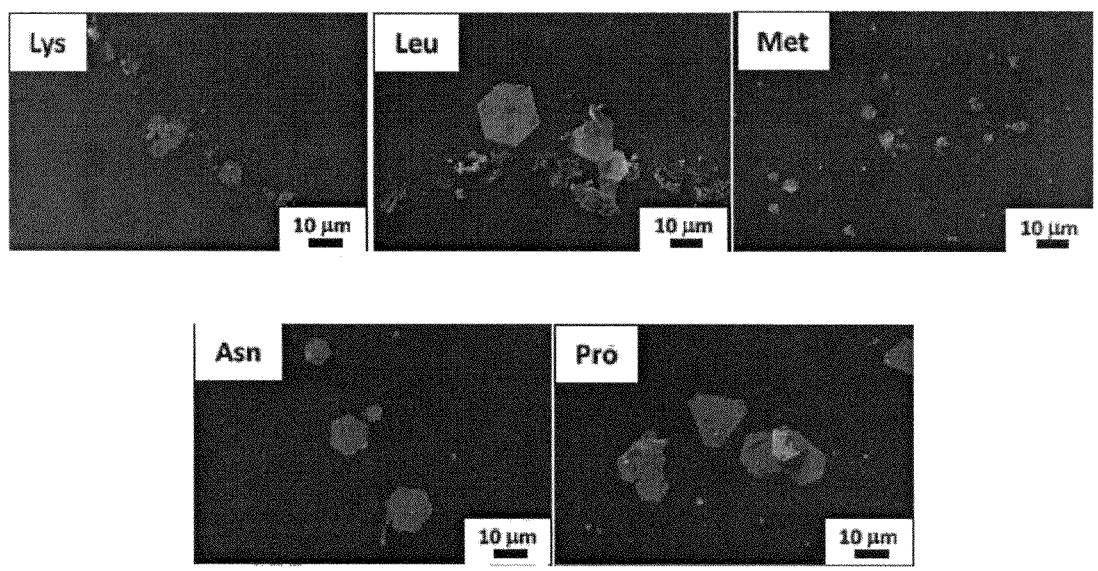
Figure 16C:
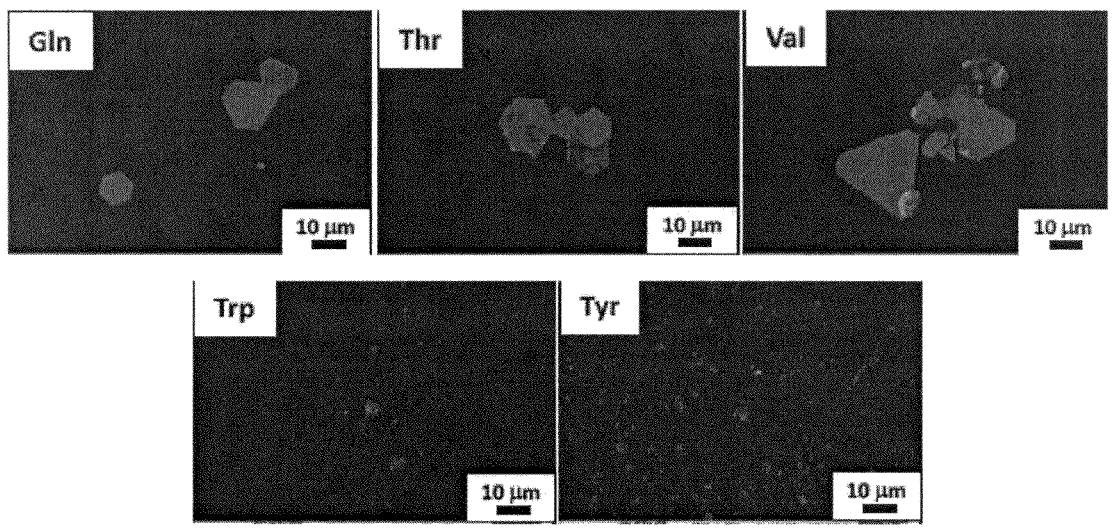
Figure 17A:
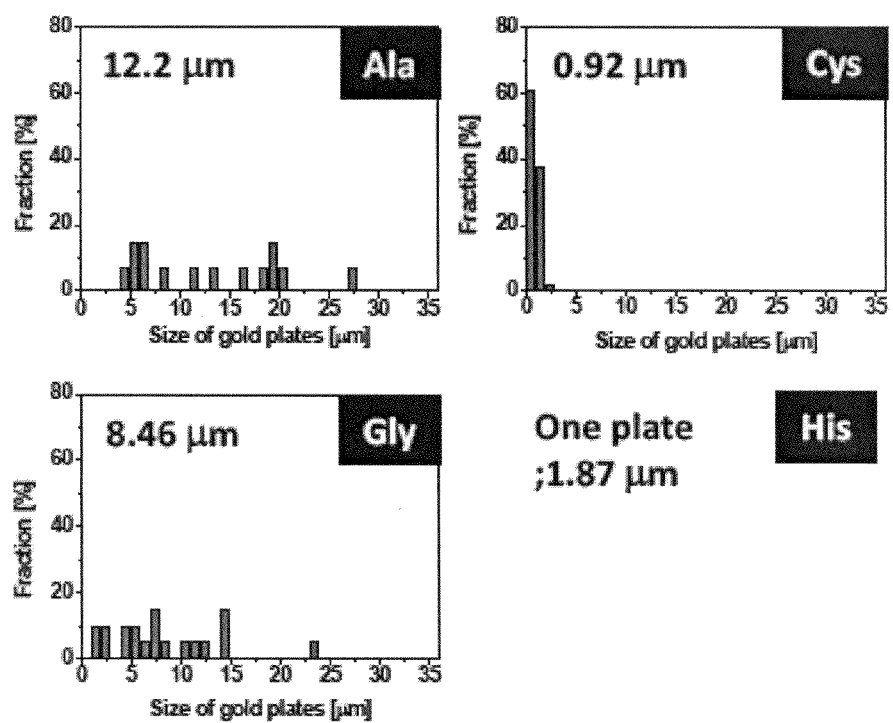
FIG. 17A-17E represent average size of the nanoplatelets as a function of 20 amino acid substitution at 11th position of Midas-11 (counting 12 to 87 plates in each sample).
Figure 17B:
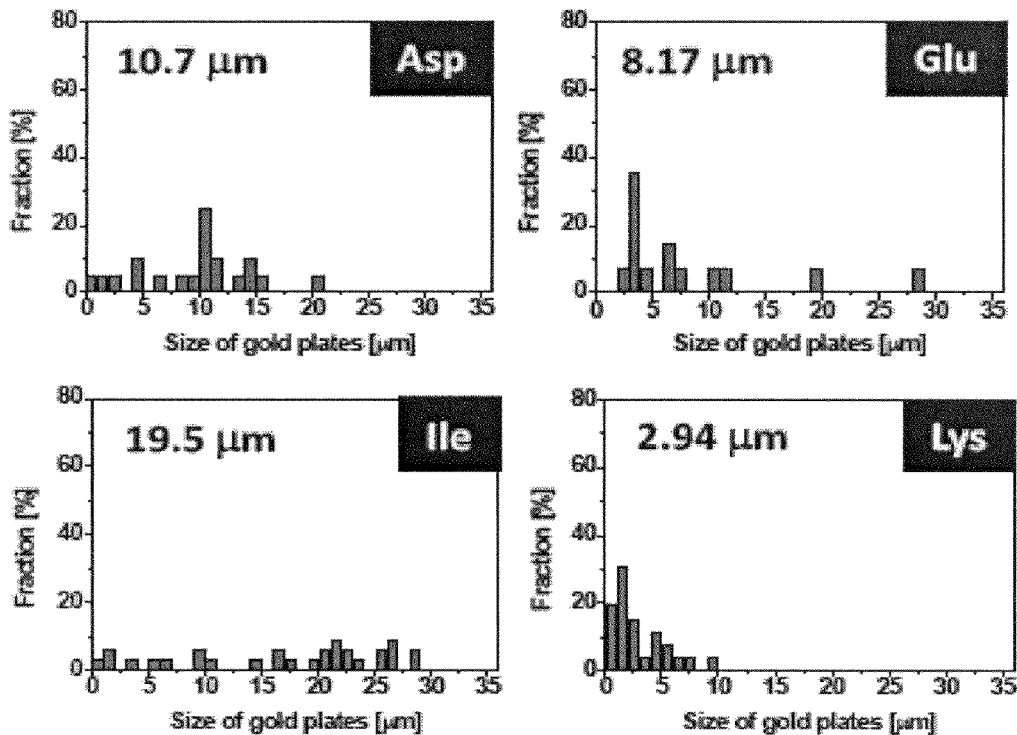
Figure 17C:
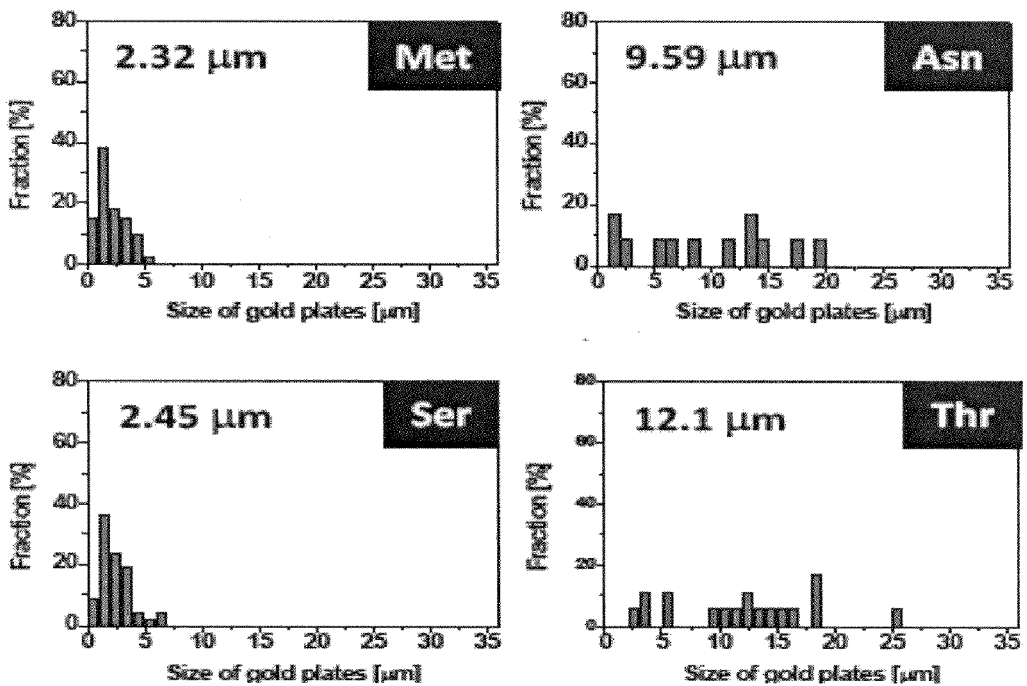
Figure 17D:
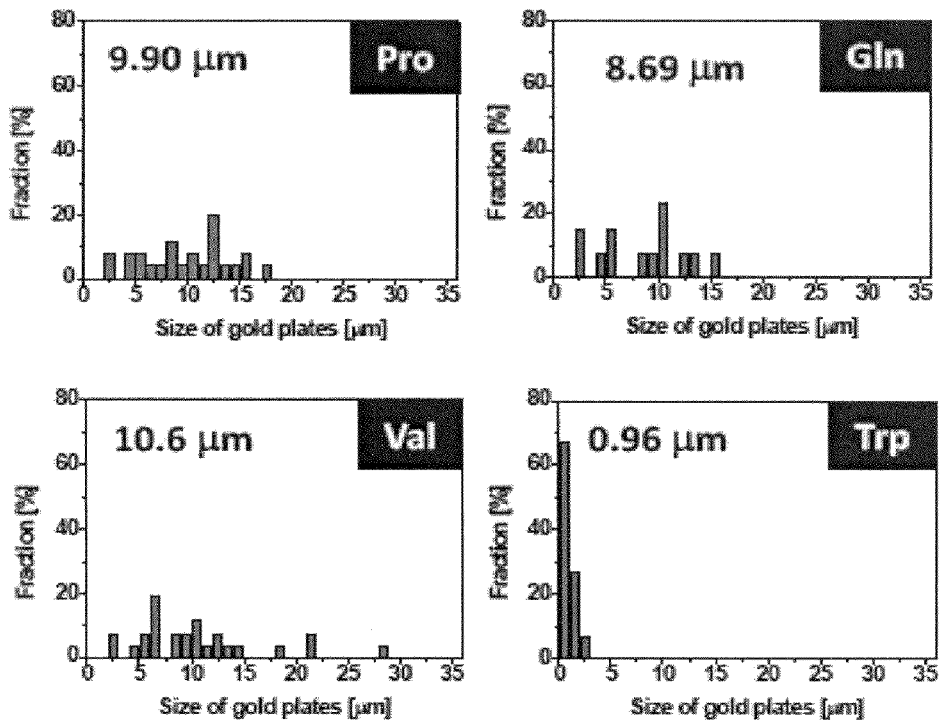
Figure 17E:
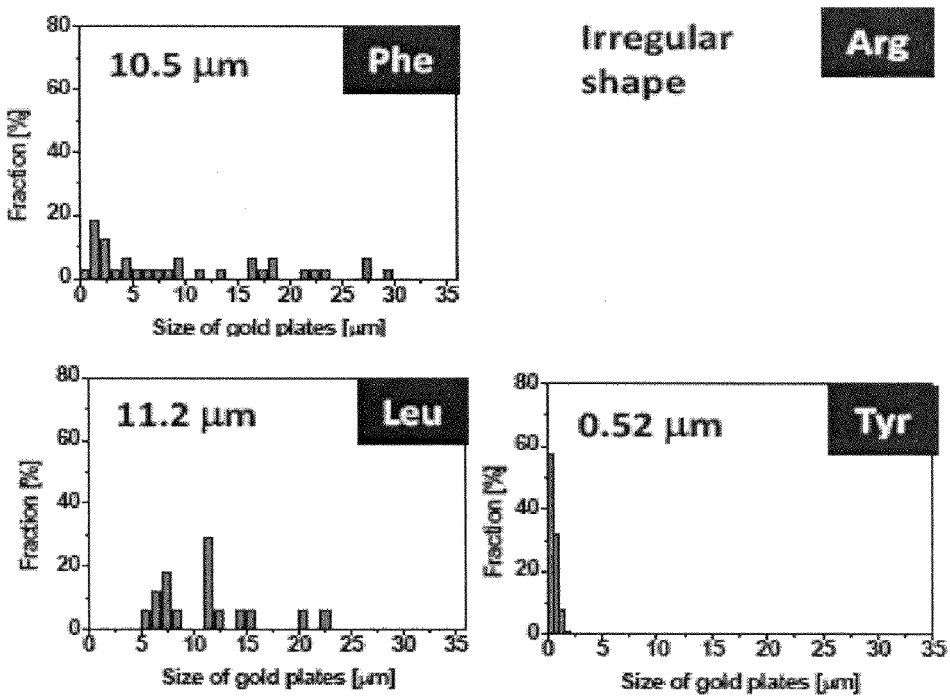
Figure 18:
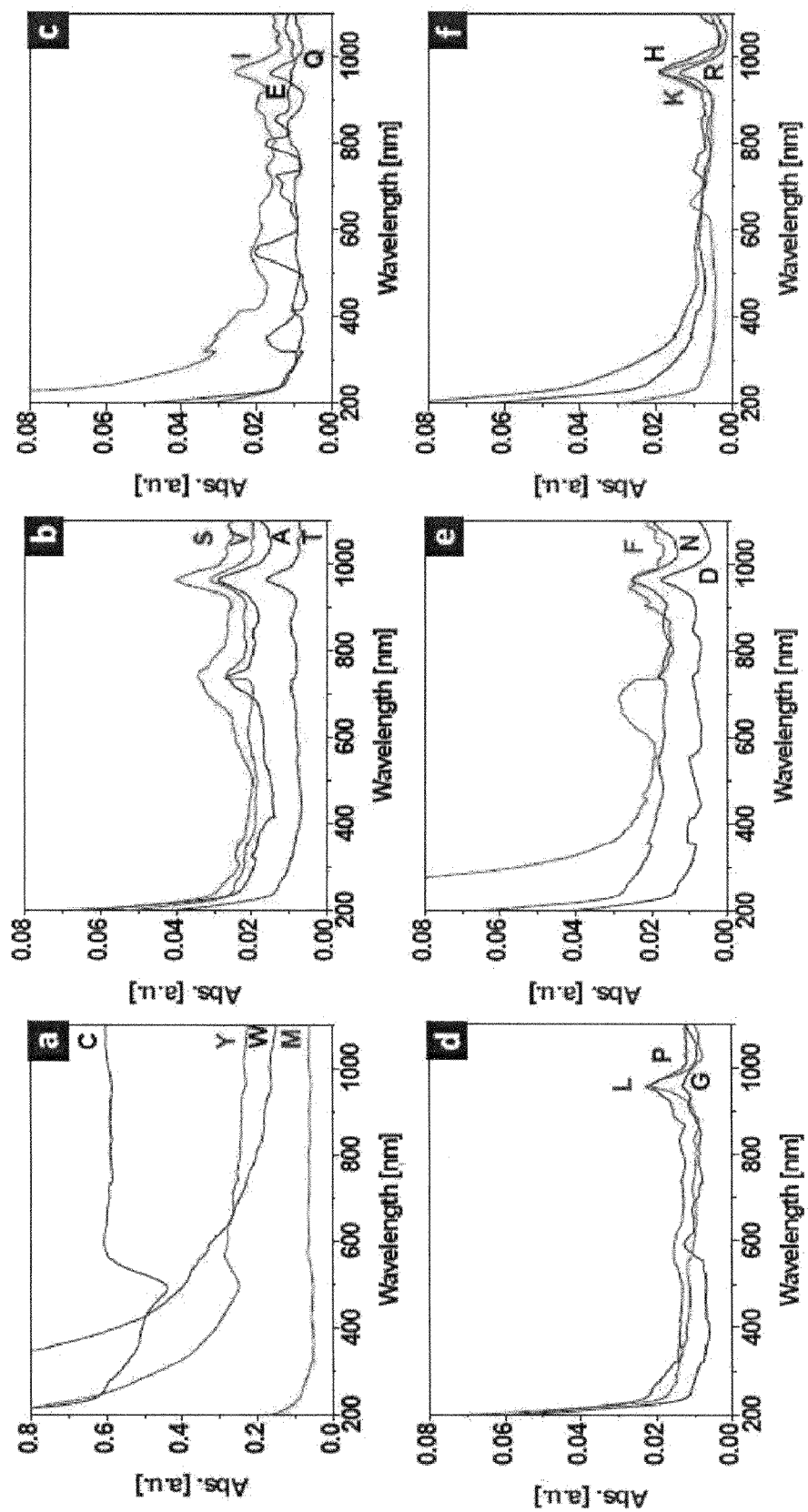
FIG. 18 represents UV-Vis spectra of the reaction solutions containing the synthesized gold nanostructures in 3 days by 20 different Midas peptides (0.2 mg/ml) with 0.5 mM HAuCl$_4$ at pH 3.0 and 37° C. in deionized water.

At low pH values below 3, the shape and size of the gold nanostructures are quite different, where large platelets are formed with hexagonal or trigonal shape. At pH<3, the nucleation rate is higher since more twinned and multiple-twinned particles are present. The size and morphology of the synthesized gold particles evolve with time of synthesis duration (FIG. 14). Synthesis experiments with incubation time of 6, 12, 24, 48, and 72 hrs were conducted in deionized water with the fixed condition of pH 3, 0.5 mM $HAuCl_4$, 0.2 mg Midas-11, and 37° C. After 6 hr incubation, the gold particles are formed in three types, (1) about 500 nm diameter of trigonal and hexagonal platelets in rare, (2) 50 to 100 nm isometric crystals of trigonal and hexagonal platelets, representing single crystals or multiple twinned crystals, (3) 2 to 5 nm of isolated shapes nanoparticles, representing most single crystals with rare twinned crystals (FIG. 14). With progress of incubation time, the large platelets with trigonal or hexagonal shapes become more abundant. Gold platelets increase in size up to 5 microns after 24 hrs and up to 20 microns after 72 hrs (FIG. 14(c)). However, the nanometer size particles decrease in abundance with time of incubation. Clearly visible inside the hexagonal plates are small holes, which in most cases have faceted outlines following the hexagonal edges of the platelets (FIG. 14(b), (c), and (d)). Also such particles exhibit overlapping hexagonal terraces which suggest screw dislocation assisted growth. As predicted by theoretical consideration (Frank, F. C., Capillary equilibria of dislocated crystals. *Acta Crystallogr.* 4, 497 (1951)) and later confirmed by experiments (Amelinckx, S., Growth spirals originating from screw dislocations on gold crystals. *Philos. Mag.* 43, 562 (1952); Suito, E. and Uyeda, N., Spiral growth of colloidal gold and moire fringe. *Nature* 185, 453 (1960)), screw dislocation growth can cause considerable strain at the core of the dislocation line. The growing crystals will tend to free themselves from the strained part, which for crystals growing in solution results in dissolving the strained region along the dislocation line and forming hollow cylinders. The fact that the trigonal and hexagonal thin platy crystals are defined by sides parallel to {121}-type faces can be understood in the light of the fact that the growth of the original isometric nuclei takes place almost in two dimensional environment controlled by the structure of the twins which can be described as a rotation around an axis normal to the (111) plane. The kinks formed at the edges of the twins are favorable nucleation sites that will facilitate the subsequent growth of the crystals (Lofton, C. and Sigmund, W., Mechanisms controlling crystal habits of gold and silver colloids. *Adv Funct. Mater.* 15, 1197 (2005)). In the (111) plane the <1-10>-type directions are parallel to rows of atoms where the distance between Au atoms is the shortest. Bonding between Au atoms along such closed packed rows will require minimum energy. This will induce preferential growth along <1-10> directions and as a consequence it will cause development of the {121} faces and disappearance of the {110} faces due to their fast growth rate. The growth rate is increased compared to the high pH conditions and large platelet crystals are formed predominantly controlled by twinned crystals and screw dislocations. Also noteworthy is the fact that the total amount of gold precipitated is low at both low and high pH. The nucleation and growth rate are both high at pH 4.5 and the twinning and defect controlled growth again take place. In addition, the peptide chains, which have high reducing activity in this condition, not only facilitate the fast nucleation process but also serve as template to bind the nuclei along its chains and cause formation of extended ribbons. The time-series experiment at pH 4.5 also clearly elucidates the growth mechanism of the gold nanoribbons. After 6 hrs of treatment (FIG. 15(a)) formation two types of crystals can be observed, the first are small 2-5 nm isometric single crystals and the second are polycrystalline aggregates in the form of twisted ribbons consisting of single crystal segments in the range of 10 to 30 nm in size. The aggregates reach lengths of 100 nm and more. After 12 hrs of treatment the product is almost uniformly long up to 1 μm long twisted ribbons made of small crystals (10-30 nm in diameter) randomly intergrown (FIG. 15(b)). After 24 and 48 hrs of synthesis the ribbons increase in length the width does not change significantly (FIG. 15(c) and (d)). The significant development at this stage is that usually one end of the ribbons develops a region with increased width, which also clearly shows single crystal character. This trend continues during the 72 hrs experiment where the ribbons become straighter and the length and width of the single crystal region at their tips increases (FIG. 6A (e) and 6B (f)). The tail of the ribbons still shows polycrystalline character which demonstrates that the conversion to single crystal ribbon is unidirectional form the "head" towards the tail.

From the time-series experiments at pH 4.5 is clear that nucleation starts in the form of small crystals randomly distributed. During the early process of crystal ripening a transformation takes place, where the isometric nuclei are aligned along the peptide chains and form twisted ribbons of individual crystals randomly joined together into a ribbon. With the progress of the reaction the twisted ribbons gradually transform to more straight chains with single crystal character. The fact that the ribbons are formed by triangular segments suggest that the growth of the nuclei is controlled by their twin structure facilitating development of platelet crystallites, which interact at a later stage to arrange themselves into single crystal ribbons by Ostwald ripening mechanism. The "head" of the ribbons develop in lateral dimension to much greater extent as compared to the body of the ribbon, most probably, due to fact the supply of Au nuclei and ad-atoms is less restricted spatially, also the development of a platy habit with exposed fast growing faces further accelerates the growth and leads to the formation of large "heads" and thin tails.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

[1] Addadi, L. and Weiner, S., Control and design principles in biological mineralization. *Angew Chem. Int Ed. Engl.* 31, 153 (1992).

[2] Steigerwald, M. L. and Brus, L. E., Synthesis, stabilization, and electronic structure of quantum semiconductor nanoclusters *Annu. Rev. Mater Sci.* 19, 471 (1989).

[3] Burda, C., Chen, X., Narayanan, R., and El-Sayed, M. A., Chemistry and properties of nanocrystals of different shapes. *Chem Rev* 105 (4), 1025 (2005).

[4] Schuler, D. and Frankel, R. B., Bacterial magnetosomes: microbiology, biomineralization and biotechnological applications. *Appl Microbiol Biotechnol* 52 (4), 464 (1999).

[5] Sweeney, R. Y. et al., Bacterial biosynthesis of cadmium sulfide nanocrystal. *Chem. Biol.* 11, 1553 (2004).

[6] Lee, J. H., Han, J., Choi, H., and Hur, H. G., Effects of temperature and dissolved oxygen on Se(IV) removal and Se(0) precipitation by *Shewanella* sp. HN-41. *Chemosphere* 68 (10), 1898 (2007).

[7] Klonowska, A., Heulin, T., and Vermeglio, A., Selenite and tellurite reduction by *Shewanella oneidensis*. *Appl Environ Microbiol* 71 (9), 5607 (2005).

[8] Shankar, S. S. et al., Biological synthesis of triangular gold nanoprisms. *Nat. Mater.* 3 (7), 482 (2004).

[9] Lengke, M. F., Fleet, M. E., and Southam, G., Biosynthesis of silver nanoparticles by filamentous cyanobacteria from a silver(I) nitrate complex. *Langmuir* 23 (5), 2694 (2007).

[10] Baesman, S. M. et al., Formation of tellurium nanocrystals during anaerobic growth of bacteria that use Te oxyanions as respiratory electron acceptors. *Appl Environ Microbiol* 73 (7), 2135 (2007).

[11] Lee, J. H. et al., Biogenic formation of photoactive arsenic-sulfide nanotubes by *Shewanella* sp. strain HN-41. *Proc. Natl. Acad. Sci. U. S. A.* 104 (51), 20410 (2007).

[12] Xie, 3. et al., Identification of active biomolecules in the high-yield synthesis of single-crystalline gold nanoplates in algal solutions. *small* 3 (4), 672 (2007).

[13] Sarikaya, M. et al., Molecular biomimetics: nanotechnology through biology. *Nature Mater.* 2, 577 (2003).

[14] Brown, S., Sarikaya, M., and Johnson, E., A genetic analysis of crystal growth. *J. Mol. Biol.* 299, 725±735 (2000).

[15] Liu, X. et al., Shape-controlled growth of micrometer-sized gold crystals by a slow reduction method. *small* 2, 1046 (2006).

[16] Daniel, M. C. and Astruc, D., Gold nanoparticles: assembly, supramolecular chemistry, quantum-size-related properties, and applications toward biology, catalysis, and nanotechnology. *Chem Rev* 104 (1), 293 (2004).

[17] Link, S. and El-Sayed, M. A., Spectral properties and relaxation dynamics of surface plasmon electronic oscillations in gold and silver nanodots and nanorods. *J. Phys. Chem. B* 103, 8410 (1999).

[18] Gole, A. et al., Pepsin-gold colloid conjugates: Preparation, characterization, and enzymatic activity. *Langmuir* 17 (5), 1674 (2001).

[19] Brown, S., Metal-recognition by repeating polypeptides. *Nat Biotech* 15 (3), 269 (1997).

[20] He, S., Zhang, Y., Guo, Z., and Gu, N., Biological synthesis of gold nanowires using extract of *Rhodopseudomonas capsulata*. *Biotechnol Prog* 24 (2), 476 (2008).

[21] Lofton, C. and Sigmund, W., Mechanisms controlling crystal habits of gold and silver colloids. *Adv. Funct. Mater.* 15, 1197 (2005).

[22] Elechiguerra, J. L., Reyes-Gasga, J., and Yacaman, M. J., The role of twinning in shape evolution of anisotropic noble metal nanostructures. *J. Mater Chem.* 16, 3906 (2006).

[23] Peelle, B. R., Krauland, E. M., Wittrup, K. D., and Belcher, A. M., Design criteria for engineering inorganic material-specific peptides. *Langmuir* 21 (15), 6929 (2005).

The sequences described herein, and as indicated by their respective sequence identification numbers, are set forth below.

```
1  Gly Gly Thr Ser Val Leu Ile Ala Thr Pro Tyr Val

2  Thr Gly Thr Ser Val Leu Ile Ala Thr Pro Tyr Val

3  Thr Gly Gly Ser Val Leu Ile Ala Thr Pro Tyr Val

4  Thr Gly Thr Gly Val Leu Ile Ala Thr Pro Tyr Val

5  Thr Gly Thr Ser Gly Leu Ile Ala Thr Pro Tyr Val

6  Thr Gly Thr Ser Val Gly Ile Ala Thr Pro Tyr Val

7  Thr Gly Thr Ser Val Leu Gly Ala Thr Pro Tyr Val

8  Thr Gly Thr Ser Val Leu Ile Gly Thr Pro Tyr Val

9  Thr Gly Thr Ser Val Leu Ile Ala Gly Pro Tyr Val

10 Thr Gly Thr Ser Val Leu Ile Ala Thr Gly Tyr Val

11 Thr Gly Thr Ser Val Leu Ile Ala Thr Pro Gly Val

12 Thr Gly Thr Ser Val Leu Ile Ala Thr Pro Tyr Gly

13 Thr Gly Thr Ser Val Leu Ile Ala Thr Pro Ala Val

14 Thr Gly Thr Ser Val Leu Ile Ala Thr Pro Arg Val

15 Thr Gly Thr Ser Val Leu Ile Ala Thr Pro Asn Val

16 Thr Gly Thr Ser Val Leu Ile Ala Thr Pro Asp Val

17 Thr Gly Thr Ser Val Leu Ile Ala Thr Pro Cys Val

18 Thr Gly Thr Ser Val Leu Ile Ala Thr Pro Gln Val
```

| | | |
|---|---|---|
| 19 | Thr Gly Thr Ser Val Leu Ile Ala Thr Pro Glu Val | |
| 20 | Thr Gly Thr Ser Val Leu Ile Ala Thr Pro His Val | |
| 21 | Thr Gly Thr Ser Val Leu Ile Ala Thr Pro Ile Val | |
| 22 | Thr Gly Thr Ser Val Leu Ile Ala Thr Pro Leu Val | |
| 23 | Thr Gly Thr Ser Val Leu Ile Ala Thr Pro Lys Val | |
| 24 | Thr Gly Thr Ser Val Leu Ile Ala Thr Pro Met Val | |
| 25 | Thr Gly Thr Ser Val Leu Ile Ala Thr Pro Phe Val | |
| 26 | Thr Gly Thr Ser Val Leu Ile Ala Thr Pro Pro Val | |
| 27 | Thr Gly Thr Ser Val Leu Ile Ala Thr Pro Ser Val | |
| 28 | Thr Gly Thr Ser Val Leu Ile Ala Thr Pro Thr Val | |
| 29 | Thr Gly Thr Ser Val Leu Ile Ala Thr Pro Trp Val | |
| 30 | Thr Gly Thr Ser Val Leu Ile Ala Thr Pro Val Val | |

What is claimed is:

1. A peptide comprising the amino acid sequence selected from the group consisting of SEQ ID NOs:1-30.

2. A method for preparing a gold nanostructure, comprising contacting a gold salt to a peptide comprising the amino acid sequence selected from the group consisting of SEQ ID NOs:1-30.

3. The method according to claim 2, wherein the gold salt is $HAuCl_4$.

4. The method according to claim 2, wherein the nanostructure is nanoparticle, nanoplate, nanoribbon, nanowire, nanorod, nanotube or nanodot.

5. The method according to claim 2, wherein the peptide comprises the amino acid sequence of SEQ ID NO:2.

* * * * *

SEQUENCE LISTING

<160> NUMBER OF SEQ ID NOS: 31

<210> SEQ ID NO 1
<211> LENGTH: 12
<212> TYPE: PRT
<213> ORGANISM: Artificial Sequence
<220> FEATURE:
<223> OTHER INFORMATION: Synthetic Construct

<400> SEQUENCE: 1

Gly Gly Thr Ser Val Leu Ile Ala Thr Pro Tyr Val
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Construct

<400> SEQUENCE: 2

Thr Gly Thr Ser Val Leu Ile Ala Thr Pro Tyr Val
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Thr Gly Gly Ser Val Leu Ile Ala Thr Pro Tyr Val
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Construct

<400> SEQUENCE: 4

Thr Gly Thr Gly Val Leu Ile Ala Thr Pro Tyr Val
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Construct

```
<400> SEQUENCE: 5

Thr Gly Thr Ser Gly Leu Ile Ala Thr Pro Tyr Val
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Construct

<400> SEQUENCE: 6

Thr Gly Thr Ser Val Gly Ile Ala Thr Pro Tyr Val
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic Construct

<400> SEQUENCE: 7

Thr Gly Thr Ser Val Leu Gly Ala Thr Pro Tyr Val
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic Construct

<400> SEQUENCE: 8

Thr Gly Thr Ser Val Leu Ile Gly Thr Pro Tyr Val
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic Construct

<400> SEQUENCE: 9

Thr Gly Thr Ser Val Leu Ile Ala Gly Pro Tyr Val
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic Construct

<400> SEQUENCE: 10

Thr Gly Thr Ser Val Leu Ile Ala Thr Gly Tyr Val
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic Construct

<400> SEQUENCE: 11
```

```
Thr Gly Thr Ser Val Leu Ile Ala Thr Pro Gly Val
1               5                   10
```

<210> SEQ ID NO 12
<211> LENGTH: 12
<212> TYPE: PRT
<213> ORGANISM: Artificial Sequence
<220> FEATURE:
<223> OTHER INFORMATION: Synthetic Construct

<400> SEQUENCE: 12

```
Thr Gly Thr Ser Val Leu Ile Ala Thr Pro Tyr Gly
1               5                   10
```

<210> SEQ ID NO 13
<211> LENGTH: 12
<212> TYPE: PRT
<213> ORGANISM: Artificial Sequence
<220> FEATURE:
<223> OTHER INFORMATION: Synthetic Construct

<400> SEQUENCE: 13

```
Thr Gly Thr Ser Val Leu Ile Ala Thr Pro Ala Val
1               5                   10
```

<210> SEQ ID NO 14
<211> LENGTH: 12
<212> TYPE: PRT
<213> ORGANISM: Artificial Sequence
<220> FEATURE:
<223> OTHER INFORMATION: Synthetic Construct

<400> SEQUENCE: 14

```
Thr Gly Thr Ser Val Leu Ile Ala Thr Pro Arg Val
1               5                   10
```

<210> SEQ ID NO 15
<211> LENGTH: 12
<212> TYPE: PRT
<213> ORGANISM: Artificial Sequence
<220> FEATURE:
<223> OTHER INFORMATION: Synthetic Construct

<400> SEQUENCE: 15

```
Thr Gly Thr Ser Val Leu Ile Ala Thr Pro Asn Val
1               5                   10
```

<210> SEQ ID NO 16
<211> LENGTH: 12
<212> TYPE: PRT
<213> ORGANISM: Artificial Sequence
<220> FEATURE:
<223> OTHER INFORMATION: Synthetic Construct

<400> SEQUENCE: 16

```
Thr Gly Thr Ser Val Leu Ile Ala Thr Pro Asp Val
1               5                   10
```

<210> SEQ ID NO 17
<211> LENGTH: 12
<212> TYPE: PRT
<213> ORGANISM: Artificial Sequence
<220> FEATURE:
<223> OTHER INFORMATION: Synthetic Construct

<400> SEQUENCE: 17

```
Thr Gly Thr Ser Val Leu Ile Ala Thr Pro Cys Val
1               5                   10
```

```
<210> SEQ ID NO 18
<211> LENGTH: 12
<212> TYPE: PRT
<213> ORGANISM: Artificial Sequence
<220> FEATURE:
<223> OTHER INFORMATION: Synthetic Construct

<400> SEQUENCE: 18

Thr Gly Thr Ser Val Leu Ile Ala Thr Pro Gln Val
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic Construct

<400> SEQUENCE: 19

Thr Gly Thr Ser Val Leu Ile Ala Thr Pro Glu Val
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic Construct

<400> SEQUENCE: 20

Thr Gly Thr Ser Val Leu Ile Ala Thr Pro His Val
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic Construct

<400> SEQUENCE: 21

Thr Gly Thr Ser Val Leu Ile Ala Thr Pro Ile Val
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic Construct

<400> SEQUENCE: 22

Thr Gly Thr Ser Val Leu Ile Ala Thr Pro Leu Val
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic Construct

<400> SEQUENCE: 23

Thr Gly Thr Ser Val Leu Ile Ala Thr Pro Lys Val
1               5                   10
```

```
<210> SEQ ID NO 24
<211> LENGTH: 12
<212> TYPE: PRT
<213> ORGANISM: Artificial Sequence
<220> FEATURE:
<223> OTHER INFORMATION: Synthetic Construct

<400> SEQUENCE: 24

Thr Gly Thr Ser Val Leu Ile Ala Thr Pro Met Val
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic Construct

<400> SEQUENCE: 25

Thr Gly Thr Ser Val Leu Ile Ala Thr Pro Phe Val
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic Construct

<400> SEQUENCE: 26

Thr Gly Thr Ser Val Leu Ile Ala Thr Pro Pro Val
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic Construct

<400> SEQUENCE: 27

Thr Gly Thr Ser Val Leu Ile Ala Thr Pro Ser Val
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic Construct

<400> SEQUENCE: 28

Thr Gly Thr Ser Val Leu Ile Ala Thr Pro Thr Val
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic Construct

<400> SEQUENCE: 29

Thr Gly Thr Ser Val Leu Ile Ala Thr Pro Trp Val
1               5                   10

<210> SEQ ID NO 30
<211> LENGTH: 12
```

-continued

```
<212> TYPE: PRT
<213> ORGANISM: Artificial Sequence
<220> FEATURE:
<223> OTHER INFORMATION: Synthetic Construct

<400> SEQUENCE: 30

Thr Gly Thr Ser Val Leu Ile Ala Thr Pro Val Val
1               5                   10

<210> SEQ ID NO 31
<211> LENGTH: 20
<212> TYPE: PRT
<213> ORGANISM: Artificial Sequence
<220> FEATURE:
<223> OTHER INFORMATION: Synthetic Construct

<400> SEQUENCE: 31

Cys Trp Met Tyr Thr Ser Ala Val Glu Gly Ile Gln Leu Pro Asn Phe
1               5                   10                  15

Asp Arg His Lys
            20
```